US006656718B2

(12) United States Patent
Begent et al.

(10) Patent No.: US 6,656,718 B2
(45) Date of Patent: Dec. 2, 2003

(54) MODIFIED CARBOXYPEPTIDASE ENZYMES AND THEIR USE

(75) Inventors: Richard H. J. Begent, London (GB); Kerry Chester, London (GB); Nigel P. Minton, Wiltshire (GB); Anthony R. Rees, Bath (GB); Surinder K. Sharma, London (GB); Daniel I. R. Spencer, Hertfordshire (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 09/898,461

(22) Filed: Jul. 5, 2001

(65) Prior Publication Data

US 2002/0090709 A1 Jul. 11, 2002

Related U.S. Application Data

(60) Provisional application No. 60/216,689, filed on Jul. 7, 2000.

(51) Int. Cl.[7] .................................................. C12N 9/48
(52) U.S. Cl. ............................................. 435/212; 514/12
(58) Field of Search ...................... 514/12, 44; 530/300; 435/320.1, 212

(56) References Cited

U.S. PATENT DOCUMENTS 5,876,691 A    3/1999  Chester et al.

FOREIGN PATENT DOCUMENTS

| EP | 0 121 352 | 10/1984 |
|---|---|---|
| EP | 0 415 731 A3 | 3/1991 |
| WO | WO 88/07378 | 10/1988 |
| WO | WO 91/02805 | 3/1991 |
| WO | WO 92/14829 | 9/1992 |
| WO | WO 93/10814 | 6/1993 |
| WO | WO 94/02450 | 2/1994 |
| WO | WO 94/21792 | 9/1994 |
| WO | WO 94/25429 | 11/1994 |
| WO | WO 95/02420 | 1/1995 |
| WO | WO 95/03830 | 2/1995 |
| WO | WO 95/07994 | 3/1995 |
| WO | WO 95/12678 | 5/1995 |
| WO | WO 95/14091 | 5/1995 |
| WO | WO 95/15341 | 6/1995 |
| WO | WO 95/24928 | 9/1995 |
| WO | WO 96/03151 | 2/1996 |
| WO | WO 96/03515 | 2/1996 |
| WO | WO 96/22277 | 7/1996 |
| WO | WO 97/26918 | 7/1997 |

OTHER PUBLICATIONS

Rowsell et al, (1997) Structure, vol. 5:337–347.
Sharma et al (1996) Transplantation proc. vol. 28:3154; Effects of cyclosporine on immunogenecity of bacterial CPG2 in ADEPT.
Cai et al, Proc. Natl. Acad. Sci. USA, vol. 92, pp. 6537–6541, Jul. 1995.
Anthony, The Biochemistry of Methylotrophs (1982), p. 269.
Bagshawe et al, Transplantation Proceedings, vol. 28, No. 6 (Dec.), 1996; pp. 3156–3158.
Sharma et al (Mar. 10, 2002) Abstract presented at AACR 2000.
Sharma et al (2000) Abstract presented at BACR 2000.
Spencer et al (2000), Abstract presented at BACR 2000.
Englehardt et al (1993) Nature Genetics, vol. 4:27–34.
Sharma et al, Br. J. Cancer (1990), 61, 659–662.
Sharma et al, Cancer (Phila.) vol. 73: 1114–20 (1994).
Springer et al, J. Med. Chem. 1990, 33, 677–681.
Springer et al, Cell Biophysics, vol. 22, 1993, 9–26.
Boxer et al, Br. J. Cancer (1994), 69, 307–314.
Stribbling et al. Cancer Chemother. Pharmacol (1997) 40:277–284.
Wilson et al. J. Mol. Biol. (1990) 211:301–303.
Huber et al, Proc. Natl. Acad. Sci. USA, vol. 88, pp. 8039–8043, Sep. 1991.
Michael et al, Ummunotechnology 2 (1996) 47–57.
Bhatia et al, Int. J. Cancer: 85, 571–577 (2000).
Burrows et al, Proc. Natl. Acad. Sci. USA, vol. 90, pp. 8996–9000, Oct. 1993.
Culver et al, Science, Vo. 256, Jun. 12, 1992, 1550–1552.
Blakey et al, Cell Biophysics, vols. 24/25, 1994, pp. 178–183.
Melton et al, Journal of the Nat. Cancer Institute, vol. 88, No. 3/4, Feb. 21, 1996.
Minton et al, Gene, 31 (1984) 31–38.
Melton et al. Eur. J. Cancer, vol. 29A, No. 29A, No. 8:1177–83.
Cooper et al, Journal of Clinical Ligand Assay, vol. 19, No. 1:80–84 (1996).
Sirkora et al, Ann. N.Y. Acad. Sci. vol. 716:pp. 115–125 (May 31, 1994).
Fox et al, Gene Therapy (1996) 3, 173–178.
Springer et al. Anti–Cancer Drug Design (1991) 6, 467–479.
Sharma et al, Cell Biophysics, vol. 21, 1992. pp. 109–120.
Bagshawe et al, Tumor Targeting (1995) 1, 17–29.

(List continued on next page.)

*Primary Examiner*—James Ketter
(74) *Attorney, Agent, or Firm*—Nixon & Vanderhye, P.C.

(57) ABSTRACT

The invention relates to improvements relating to cancer therapy based on the identification of a number of regions of CPG2 which contain epitopes which appear to be involved in the production of a host immune response and which may be modified to alter the immunogenicity in patients. Production of fusions of CPG2 with an antibody, where the CPG2 protein has been tagged provides a CPG2 protein which has reduced immunogenicity. By using partially glycosylated enzyme obtainable by *P. pastoris* expression, the efficacy of antibody-CPG2 fusions is enhanced.

10 Claims, 18 Drawing Sheets

OTHER PUBLICATIONS

McCullough et al, The Journal of Biological Chemistry, vol. 246, No. 23, Dec. 10, 1971; pp. 7207–7213.

Rodrigues et al, Cancer Research 55, 63–70. Jan. 1, 1995.

Bagshawe et al, Antibody, Immunoconjugates, and Radiopharmaceutials, vol. 4, No. 4, 1991, pp. 915–925.

Sharma et al, Disease Markers, vol. 9, 225–231 (1991).

Bosslet et al. Cancer Research 54, 2151–2159, Apr. 15, 1994.

Eccles et al, Cancer Research 54, 5171–5177, Oct. 1, 1994.

Blakey et al, Cancer Research 56, 3287–2392, Jul. 15, 1996.

Spencer et al (1996) Brit. J. Cancer. 80 suppl. vol. 2. p. 52.

Napier et al. Clinical Cancer Research, vol. 6, 765–772, Mar. 2000.

Springer et al, Eur. J. Cancer, 27, 1361–66. 1991.

Melton et al, Journal of Immunological Methods, 158 (1993) 49–56.

Figure 3b

| | | |
|---|---|---|
| 1 | MRPSIHRTAIAAVLATAFVAGTALAQKRDN | 30 |
| 31 | VLFQAATDEQPAVIKTLEKLVNIETGTGDA | 60 |
| 61 | EGIAAAGNFLEAELKNLGFTVTRSKSAGLV | 90 |
| 91 | VGDNIVGKIKGRGGKNLLLMSHMDTVYLKG | 120 |
| 121 | ILAKAPFRVEGDKAYGPGIADDKGGNAVIL | 150 |
| 151 | HTLKLLKEYGVRDYGTITVLFNTDEEKGSF | 180 |
| 181 | GSRDLIQEEAKLADYVLSFEPTSAGDEKLS | 210 |
| 211 | LGTSGIAYVQVNITGKASHAGAAPELGVNA | 240 |
| 241 | LVEASDLVLRTMNIDDKAKNLRFNWTIAKA | 270 |
| 271 | GNVSNIIPASATLNADVRYARNEDFDAAMK | 300 |
| 301 | TLEERAQQKKLPEADVKVIVTRGRPAFNAG | 330 |
| 331 | EGGKKLVDKAVAYYKEAGGTLGVEERTGGG | 360 |
| 361 | TDAAYAALSGKPVIESLGLPGFGYHSDKAE | 390 |
| 391 | YVDISAIPRRLYMAARLIMDLGAGK | 415 |

MODIFIED CARBOXYPEPTIDASE ENZYMES AND THEIR USE

This application claims benefit of U.S. Provisional Application No. 60/216,689, filed Jul. 7, 2000, the entire contents of which is hereby incorporated by reference.

FIELD OF THE INVENTION

The present invention relates to improvements to the enzyme carboxypeptidase G2, and the use of this enzyme in therapy, particularly antibody-directed enzyme prodrug therapy (ADEPT) and gene-directed enzyme prodrug therapy (GDEPT).

BACKGROUND TO THE INVENTION

Over the years, many cytotoxic compounds have been discovered which are of potential use in cancer chemotherapy. For example, nitrogen mustards form one important family of such cytotoxic compounds. A problem with the clinical use of cytotoxic compounds is in achieving sufficient selectivity in the cytotoxic effect between tumour cells and normal cells. One approach to address this problem has involved the development of so-called prodrugs which are derivatives of the cytotoxic drug, often relatively simple derivatives, whose cytotoxic properties are considerably reduced compared to those of the parent drugs. Numerous proposals have been made for the administration of such prodrugs to patients under regimes whereby the prodrug is only converted by the action of an enzyme to the cytotoxic drug in the region of the intended site of action.

A variety of systems exist for delivery of the enzyme. One such system is described in WO88/07378, and involves conjugating the enzyme to an antibody specific for a tumour marker, delivering the antibody enzyme conjugate to a patient, allowing the conjugate to localise, and then delivering the prodrug to the patient. This system is referred to as antibody-directed enzyme prodrug therapy" (ADEPT).

Another approach for delivery of the enzyme to the desired site of action is by the use of a genetic construct, such as a viral or non-viral vector carrying a gene encoding the prodrug-converting enzyme, which is delivered to cells at the desired site of action (Huber et al, Proc. Natl. Acad. Sci. USA (1991) 88, 8039). A further alternative system is to provide a ligand, generally a naturally occurring polypeptide whose biological role involves its binding to a cognate receptor on the surface of the cell, conjugated to the prodrug-activating enzyme. This system, LIDEPT, is described in WO/97/26918, where VEGF is particularly exemplified as an example of a ligand. A further alternative system is to use bacterial delivery systems, for example, Clostridium or Salmonella based systems, in which bacteria selectively colonise tumours. A Clostridium based system is described in, for example, Fox et al, 1996 Gene Therapy 3 173–178.

One class of prodrugs suggested for use in the above systems is that of prodrugs of nitrogen mustard compounds. Benzoic acid nitrogen mustards are bifunctional alkylating agents, and a variety of prodrugs of such compounds are described in the art. One class of such prodrugs comprise a protecting group which may be removed by the action of a carboxypeptidase enzyme, such as bacterial carboxypeptidase G, particularly the Pseudomonas-derived enzyme carboxypeptidase G2 (CPG2). CPG2 is a well characterised enzyme with no mammalian equivalent. It is a non-covalently associated, homo-dimeric, metalloenzyme which cleave the C-terminal glutamic acid of folate to yield a pteroate derivative. This has been exploited to cleave glutamic acid from a variety of prodrugs to release potent nitrogen mustard compounds.

Examples of prodrugs which may be activated by CPG2 are described in, for example, Springer et al., Anti-Cancer Drug Design (1991) 6; 467–479, WO88/07378, WO94/25429 and WO96/22277. Fusions of an antibody fragment directed against carcinoembryonic antigen (CEA) with CPG2 have been described in Michael et al, Immunotechnology 2 47–57 (1996) and the use of this fusion in in vivo model systems has been described in Bhatia et al, Int. J. Cancer, 85; 571–577 (2000).

A feature of CPG2 is that being a bacterial enzyme, it does not occur naturally in the body of a human patient, and thus prodrugs designed to be activated by this enzyme will not be activated elsewhere in the patient. However, the drawback to this feature is that the enzyme provokes an immune response in a patient, and indeed such responses have been observed in clinical trials of ADEPT using CPG2 (Sharma et al, 1992, Cell Biophys., 21;109–120; Bagshawe et al, 1995, Tumour Targeting, 1; 17–30).

DISCLOSURE OF THE INVENTION

We have investigated the immunogenicity of CPG2 and identified a number of regions of this enzyme which contain epitopes which appear to be involved in the production of a host immune response. We have found that where a host immune response is caused by the presence of such epitopes, these epitopes may be modified to alter the immunogenicity in patients. However the invention is not limited to this aspect alone, since modifications to these epitopes may be provided which render the CPG2 less reactive with sera from CPG2 immunised patients. The latter aspect of the invention is also advantageous, to allow the development of CPG2 fusions which "escape" or "evade", to a greater or lesser degree, an immune response of a host which has been provoked by a wild-type CPG2 or another altered form of CGP2 which has a set of one or more epitope modifications which cause an established host response to a previously administered form of CGP2 to be less effective against the newly altered form.

Throughout this text where specific amino acids or amino acid sequences of the Pseudomonas CPG2 used in the examples below are referred to we have used the numbering used in the Swiss Prot database entry for CPG2 (accession number p06621). The unprocessed form of CPG2 has a sequence 415 amino acids long. The first 22 residues of this sequence are removed in the processed form of CPG2. In the MFE-23::CPG2 fusion protein described here, the first amino acid of the CPG2 domain is amino acid 25 according to the Swiss Prot CPG2 entry.

In a first aspect, the invention provides a CPG2 enzyme in which an immunogenic region selected from:
KIKGRGGK (amino acids 98–105, SEQ ID NO:1)
KEYGVRD (157–163, SEQ ID NO:2), preferably YGVRD (159–163 (SEQ ID NO:6))
KLADY (191–195, SEQ ID NO:3)
GAGK (412-C-terminal(415), SEQ ID NO:4), preferably AG (413–414),
EGGKKLVDK (331–338, SEQ ID NO:5)
is modified to reduce or alter immunogenicity to a mammalian immune system whilst retaining CPG2 activity.

In another aspect, we have also found that production of fusions of CPG2 with an antibody, where the CPG2 protein has been tagged provides a CPG2 protein which has reduced immunogenicity. Thus in a further aspect of the invention, there is provided a CPG2 enzyme, including any of those of the first aspect, which is tagged with a his or myc-his tag.

There is also provided by the invention methods of treatment or diagnosis by methods such as ADEPT, GDEPT or LIDEPT which utilise the CPG2 of the present invention. These and other aspects of the invention are described herein in more detail below.

DESCRIPTION OF THE DRAWINGS

FIG. 3B shows the amino acid sequence of CPG2 (SEQ ID NO:7).

DETAILED DESCRIPTION OF THE INVENTION

Figure 1:
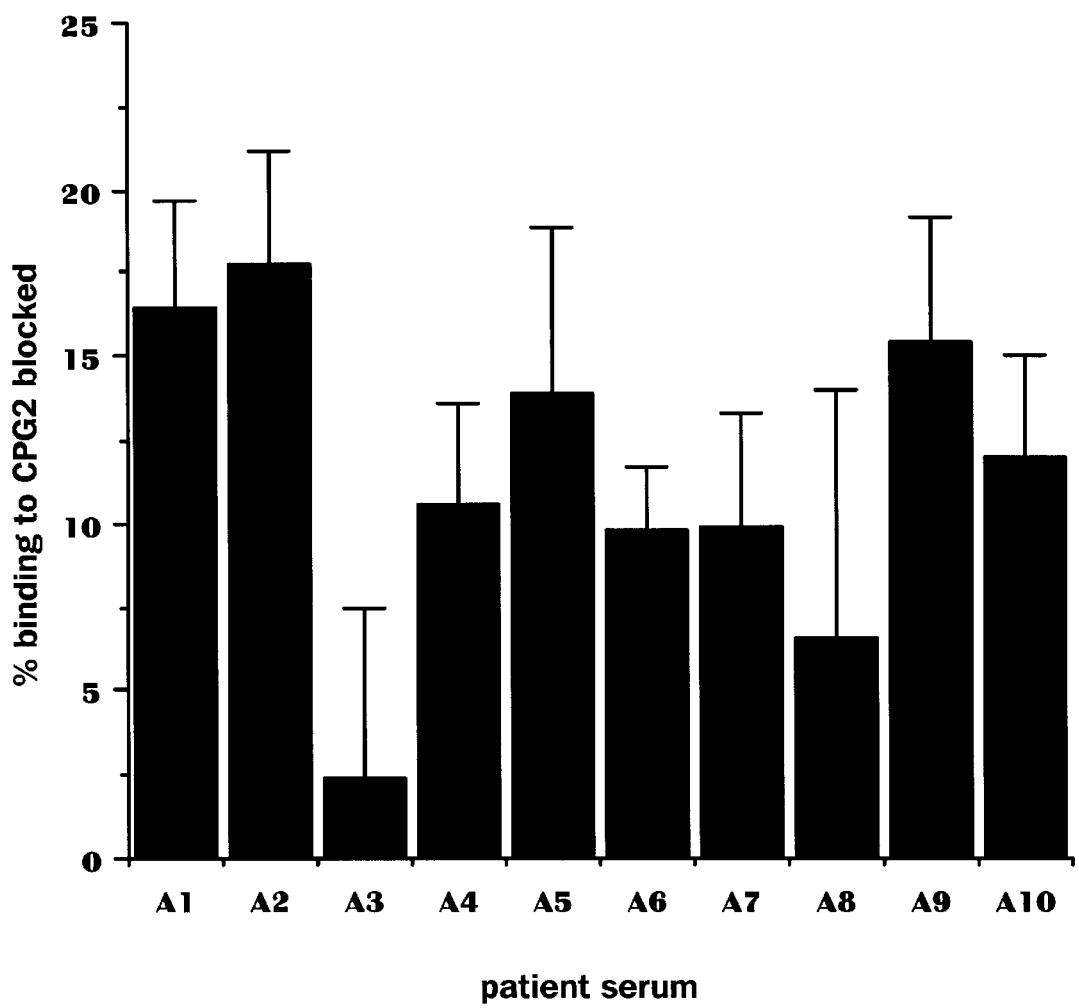
FIG. 1 illustrates inhibition of CPG2 binding of human antibodies by CM79 determined by ELISA. Sera A1 to A10 were from ten patients post treatment with an A5B7-CPG2 antibody-enzyme conjugate used in an ADEPT clinical trial. Values are mean±SEM.

The modifications to the immunogenic regions identified above may be any type of modifications which have the defined function of retaining CPG2 activity and being reduced or altered in immunogenicity. These are essentially functional tests which those of skill in the art can perform using routine skill and knowledge.

Thus for example, CPG2 activity may be tested by the ability of the enzyme to hydrolyse methotrexate (MTX). CPG2 hydrolysis of MTX results in a change in absorbance at 320 nm which may be measured by spectrophotometry. CPG2 catalytic activity in solid tissues can be assayed using an indirect HPLC method, measuring, for example, 2,4-diamino-N$^{10}$ methypteroic acid (DAMPA, a metabolite of MTX). Examples of further tests are described in McCulloch et al, J. Biol. Chem. 246:7207–7213, 1971 and Sherwood et al, Eur. J. Biochem. 148: 447–453, 1985.

The reduction or alteration in immunogenicity of the modified enzyme may be determined by injecting the enzyme into a test animal, typically a mouse, and assaying the immune response of the mouse to one or more—e.g. 2, 3, 4 or 5 repeat injections of the modified enzyme compared to an unmodified control. Such a protocol is exemplified in the accompanying examples, and may be used in similar form.

Particular modifications include:

substitutions deletions insertions replacement of the immunogenic regions by human sequences of sequence in particular at positions where intramolecular interactions are observed to be present in the X ray structure.

These replacements may be made to retain the correct stereochemistry, hydrophobicity or charge characteristics, even where sequence similarity may be low.

Examples of substitutions include the replacement of charged residues for uncharged residues, uncharged residues for charged residues, polar residues for non-polar residues, non-polar residues for polar residues, large side chain residues for smaller side chain residues, small side chain residues for larger side chain residues. Specific residues that may be substituted include R162 and G412. Other CPG2 amino acids to be substituted will be identified using anti-CPG2 antibodies/antibody fragments particularly where these can block human anti-CPG2 antibodies as identified using enzyme linked immunosorbent assay (ELISA). These anti-CPG2 antibodies will be epitope mapped. Subsequent substitution of amino acids in these CPG2 epitopes will be of those type mentioned.

The MFE-23::CPG2-his fusion protein has a hexa-His tag at the C-terminus of CPG2. This tag may be extended by inserting sequences of varying length between the hexa-His tag and the C-terminus of CPG2. Insertions include the myc tag (EQKLISEEDLN (SEQ ID NO:8)) to result in a myc-his tag having the sequence AAASFLEQKLISEEDLNSAVDH-HHHHH (SEQ ID NO:9), or a humanized version of the myc tag. Such insertions may serve to mask immunogenic surfaces on the CPG2 protein.

Usually, no more than 10, for example from 5 to 10, such as 5, preferably no more than 4, for example 3, 2 or just one substitution will be made to the native CPG2 sequence in each of the immunogenic regions identified. The enzyme may comprise 1, 2, 3, 4 or from 5 to 10 substituted immunogenic regions.

Similarly, no more than 10, for example from 5 to 10, such as 5, preferably no more than 4, for example 3, 2 or just one deletion will be made to the native CPG2 sequence in each of the immunogenic regions identified. The enzyme may comprise 1, 2, 3, 4 or from 5 to 10 immunogenic regions carrying a deletion.

Likewise, no more than 10, for example from 5 to 10, such as 5, preferably no more than 4, for example 3, 2 or just one insertion will be made to the native CPG2 sequence in each of the immunogenic regions identified. The enzyme may comprise 1, 2, 3, 4 or from 5 to 10 immunogenic regions in which an insertion has been made. Examples of insertions include the replacement of surface loops, extensions of either the C-terminus or the N-terminus or the replacement of any segmented sequence where the exposed residues may be substituted for other residues but where the buried residues are conserved so as to minimise disruption of the 3-D structure.

In the case of the C-terminal immunogenic region, the modification may be by way of an extension to the C-terminus of the enzyme. We have surprisingly found that addition of a polyhistidine tag to the C-terminus of CPG2 provided a significant reduction in immunogenicity. The further addition of a myc tag to the polyhistidine tag provided a further decrease.

The histidine tag is a synthetic tag widely used in the art to aid protein purification or identification. It is not a native human or murine epitope and it is therefore surprising that its addition is beneficial in reducing the immune response. The myc tag is derived from the c-myc proto-oncogene and would normally not be expected to provoke a response in its native conformation in humans.

C-terminal extensions may thus be selected broadly, although in general terms such extensions will typically be short peptide sequences of, for example, from 5 to 20 amino acids, and may be synthetic sequences or natural sequences of mammalian, particularly human origin. Two or more, such as from 2 to 5 such sequences (which may be the same or different) may be added in tandem.

Replacement of these immunogenic regions may be by human sequences of similar sequence to the wild type sequence, or by sequences exhibiting similar conformations, or by sequences exhibiting similar hydrophobic, charge, stereochemical or surface exposure characteristics. In an example procedure, the sequence, conformation and interior protein contact profile of an immunogenic region would be encoded as a set of criteria on which to search and select similar regions from a database of human protein three-dimensional structures (for example, the protein databank (PDB) could be searched using the IDITIS software (Oxford Molecular plc, UK)). Such selected regions would then be ranked on their similarity to the above criteria and the most similar sequence or sequences used for replacement of an existing immunogenic region. Where the humanised sequences comprise the same or similar residues involved in internal packing interactions as the wild type sequence, the humanised sequence may not require further modification. If, however, these residues result in structural perturbations of the internal interactions with the rest of the molecule, these buried residues may be substituted with residues present in the wild-type molecule, producing a hybrid sequence which retains internal packing interactions and stereochemistry. Examples of suitable regions found using this method for replacement of the KEYGVRD sequence (SEQ ID NO:2) include the hybrid sequence (maintaining intramolecular contacts) YEYGVMK (SEQ ID NO:10) of the humanised sequence YEVGMMK (SEQ ID NO:11). Examples of suitable sequences for replacement of KLADY (SEQ ID NO:3) include the hybrid sequence (maintaining intramolecular contacts) RNSDY (SEQ ID NO:12) of the humanised sequence RNSDR (SEQ ID NO:13).

In a related aspect of the invention, we have found that expression of MFECPG2 in *Pichia pastoris* provides advantages over bacterially produced CPG2. The enzyme CPG2 is bacterial and thus in its native form is not glycosylated. However, the sequence of the enzyme contains three motifs Asn-Xaa-Thr/Ser which are recognised by eukaryotic cells as targets for N-linked glycosylation, (1), (2) and (3). These three Asn residues which are glycosylated are found at positions 222, 264 and 272 of Pseudomonas CPG2. As mentioned above, CPG2 is a homo-dimer and it has been found that N-linked glycosylation appears to interfere with the formation of the dimer, particularly at its second position, 264.

Surprisingly, we have found that production of the enzyme in *P. pastoris* results in glycosylation only at residues 222 and 272, thus reducing the interference caused by glycosylation at 264 which occurs in CPG2 produced in, for example, mammalian cells.

We have also found that by using partially glycosylated enzyme obtainable by *P. pastoris* expression, the efficacy of antibody-CPG2 fusions is enhanced, in that the enzyme localises to the tumour whilst being cleared efficiently from other organs and the bloodstream of the mammalian body.

Thus the invention provides a CPG2 enzyme which is partially N-linked glycosylated at one or both of positions (1) and (3), and not N-linked glycosylated at position (2). Preferably, position (2) retains its native sequence and is not glycosylated as a result of expression in *P. pastoris*.

Expression of the CPG2 wherein the motifs (1), (2) and (3) are all present is preferably in a *P. pastoris* host cell, or a host cell of a yeast, such as a methylotrophic yeast. Such yeasts are those which are capable of growth on methanol and include yeast of the genera Hansenula, Candida, Kloeckera, Pichia, Saccharomyces, Torulopsis and Rhodotorula. A list of specific species which are exemplary of this class of yeasts may be found in C. Anthony, *The Biochemistry of Methylotrophs,* 269 (1992). Pichia, particularly *P.pastoris*, is preferred.

In the present invention, a preferred CPG2 enzyme which is used is the CPG2 whose sequence is disclosed in WO88/07378 and herein in FIG. 3B, the disclosure of which is incorporated herein by reference. However, other bacterial carboxypeptidase enzymes may be used, e.g., CPG2 enzymes from Variovorax species such as *Variovorax paradoxis* and CPG2 enzymes from other Pseudomonas species such as *Pseudomonas aeruginosa, Pseudomonas cepacia, Pseudomonas fluorescens, Pseudomonas putida, Pseudomonas syringae, Pseudomonas savastanoi,* which in the native form comprise three asparagine residues, Asn (1), Asn (2), Asn (3) numbered in the N-terminal to C-terminal direction, the residues being part of motifs which on expression in a mammalian cell are subject to N-linked glycosylation. In such enzymes Asn (1), Asn (2) and Asn (3) will be at positions homologous to Asn 222, Asn 264 and Asn 272, although they may have different positional numbering. However, Asn (1), Asn (2) and Asn (3) of these enzymes can readily be identified by persons skilled in the art, for example using sequence alignments to compare a sequence with the sequence shown herein, and thereby identify the Asn residues which correspond to Asn 222, Asn 264 and Asn 272 of FIG. 3B. Likewise, the epitopes identified as SEQ ID NOS: 1 to 5 above may have different positional numbering and/or minor modifications to the wild type sequence but can be determined by those skilled in the art by the modelling techniques described herein by analogy to FIG. 3B. CPC2 enzymes from other species of Pseudomonas may be obtained by routine cloning methodology. For example, a library of cDNA from a Pseudomonas species may be made and probed with all or a portion of the sequence of FIG. 3B under conditions of medium to high stringency.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5–1.0% SDS, 100 µg/ml denatured, fragmented salmon sperm DNA, 0.05% sodium pyrophosphate and up to 50% formamide. Hybridization is carried out at 37–42 C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37 C. in 1×SSC and 1% SDS; (4) 2 hours at 42–65 C. in 1×SSC and 1% SDS, changing the solution every 30 minutes.

Clones identified as positive may be examined to identify open reading frames encoding homologues of the sequence shown in FIG. 3B. It may be necessary to combine more than one clone to achieve a full length open reading frame, as would be understood by the person skilled in art. Clones may then be expressed in a heterologous expression system, e.g. in bacteria or yeast and the protein purified by techniques known in the art.

Alternatively, CPG2 enzyme producing bacteria may be identified by methods involving the identification of organisms that convert folic acid to pteroate or of organisms capable of growing on media with folic acid as the sole carbon source.

Suitable enzymes to which mutations according to the invention may be applied include carboxypeptidase enzymes which are mutants, variants, derivatives or alleles of the sequence shown in FIG. 3B. A carboxypeptidase enzyme which is a variant, allele, derivative or mutant may have an amino acid sequence which differs from that given in FIG. 3B by one or more of addition, substitution, deletion and insertion of one or more amino acids, for example from 1 to 20, such as from 1 to 10, e.g., 1, 2, 3, 4, 5 or 6–10 substitutions deletions or insertions.

Preferred such carboxypeptidases will have the ability to hydrolyse methotrexate (MTX). Alteration of sequence may change the nature and/or level of activity and/or stability of the carboxypeptidase enzyme.

A polypeptide which is an amino acid sequence variant, allele, derivative or mutant of the amino acid sequence shown in FIG. 3B may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. The sequence may share greater than about 60% similarity, greater than about 70% similarity, greater than about 80% similarity or greater than about 90% similarity with the amino acid sequence shown in FIG. 3B. Amino acid similarity is generally defined with reference to the algorithm GAP (Genetics Computer Group, Madison, Wis.) as noted above, or the TBLASTN program, of Altschul et al. (1990) J. Mol. Biol. 215: 403–10. Parameters employed are the default ones: for nucleotide sequences—Gap Weight 50, Length Weight 3, Average Match 10.000, Average Mismatch 0.000; for peptide sequences—Gap Weight 8, Length Weight 2, Average Match 2.912, Average Mismatch –2.003. Peptide similarity scores are taken from the BLOSUM62 matrix. Also useful is the TBLASTN program, of Altschul et al. (1990) *J. Mol. Biol.* 215: 403–10, or BestFit, which is part of the Wisconsin Package, Version 8, September 1994, (Genetics Computer Group, 575 Science Drive, Madison, Wis. USA, Wisconsin 53711). Sequence comparisons may be made using FASTA and FASTP (see Pearson & Lipman, 1988. Methods in Enzymology 183: 63–98). Parameters are preferably set, using the default matrix, as follows: Gapopen (penalty for the first residue in a gap): –12 for proteins/–16 for DNA; Gapext (penalty for additional residues in a gap): –2 for proteins/–4 for DNA; KTUP word length: 2 for proteins/6 for DNA.

Sequence comparison may be made over the full-length of the relevant sequence shown herein, or may more preferably be over a contiguous sequence of about or greater than about 20, 25, 30, 33, 40, 50, 67, 133, 167, 200, 233, 267, 300, 333, or more amino acids or nucleotide triplets, compared with the relevant amino acid sequence or nucleotide sequence as the case may be.

In further aspects the invention provides a nucleic acid encoding such modified bacterial carboxypeptidases or vectors comprising such nucleic acid. The vector is preferably an expression vector, wherein said nucleic acid is operably linked to a promoter compatible with a host cell. The invention thus also provides a host cell which contains an expression vector of the invention.

Host cells of the invention may be used in a method of making a carboxypeptidase enzyme of the invention as defined above which comprises culturing the host cell under conditions in which said enzyme or fragment thereof is expressed, and recovering the enzyme in substantially isolated form. The enzyme may be expressed as a fusion protein.

Host cells may be used to provide fusions of antibody-enzyme conjugates for use in ADEPT therapy, for ligand-enzyme conjugates for LIDEPT therapy, or may be used in the provision of vectors such as viral vectors for GDEPT therapies. ADEPT therapy has utility in the treatment of tumours which are associated with tumour specific markers, which may be the target for an antibody. By "antibody", this is intended to refer to any binding fragment thereof, characterised by the presence of a VH, and preferably also a VL region. Such fragments include single chain Fv and Fab fragments.

Examples of tumour antigens include CEA, a cell surface glycoprotein strongly expressed by most colorectal tumours. Colorectal cancer is the second leading cause of cancer death in the UK. Conventional treatments remain unable to cure patients with advanced or metastatic disease. CEA is a suitable target for ADEPT because, with highly specific antibodies, CEA is only detectable on tumours and on the luminal surface of the gut which is not readily accessible to IgG antibodies. A particular anti-CEA antibody is MFE-23 which is disclosed in WO95/15341. Other antibody chemical conjugates with CPG2 which have been proposed for ADEPT therapy are the anti-human chorionic gonadotropin monoclonal antibody (MAb) W14 F(ab')2 and the anti-c-erbB2 MAb ICR12 (Bagshawe, 1998, Tumor targeting, 3: 21–24, 1998) and the CPG2 of the present invention may be used in such conjugates.

More generally however, for ADEPT it is not essential that the target antigen is attached to the cell surface, as prodrug can be converted to active drug in the tumour interstitial space and diffuse into the tumour cells. Targets that are secreted or cleaved from tumour cells, or produced in tumour stroma, may be applicable. A target which is heterogeneously expressed, as often occurs with tumour antigens, is similarly acceptable.

Thus other targets which exist include for example the idiotype in lymphomas or mutant cell-surface proteins, which are increasingly being identified, in other tumours [Urban J L and Schreiber H, (1992) Tumour antigens. Ann Rev Immunol 10, 617–644.] relative abundance may give adequate selectivity for ADEPT although the normal tissue reactivity should be well defined. In some cases the forms expressed in normal tissue may be relatively inaccessible to antibody, as for example with CEA discussed above.

Another target which has been investigated is $p185^{HER2}$ which is upregulated in breast cancer. This antigen is also expressed on a variety of normal epithelial cells but in vitro experiments have shown that the relative abundance of $p185^{HER2}$ on a breast tumour cell line was sufficient to allow specific targeting in ADEPT [Rodrigues M L, et al,(1995) Cancer Res. 55, 63–70]. Where antigens are expressed in normal tissues their pattern of distribution should be considered when choosing a suitable toxic agent. For example, the enzyme β-lactamase, genetically fused to anti-$p185^{HER2}$, has been used to generate the drug doxorubicin for which heart tissue is a site of chronic and dose limiting toxicity and bone marrow is a site of acute toxicity. As there is no detectable expression of $p185^{HER2}$ in heart or bone marrow the above ADEPT combination seems particularly suitable for this antigen.

Tumour vasculature is an attractive target for some antibody therapies as it is readily accessible and essential for tumour growth. Moreover, experimental models have demonstrated the potential efficacy of targeted immunotoxins to kill tumour endothelial cells [Burrows F J and Thorpe P E,(1993) Proc Natl Acad Sci USA 90, 8996–9000]. Tumour vasculature may provide a good target for ADEPT if the prodrug is designed to have a very short half life so that active drug does not leak back into normal tissues via the blood.

Suitable viral vectors for VDEPT include those which are based upon a retrovirus. For GDEPT, a wide variety of vectors are available. These include those which are based upon a retrovirus. Such vectors are widely available in the art. Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described above for MLV.

EP-A-415 731 describes molecular chimeras comprising a promoter which may be activated in a tumour cell operably linked to a heterologous gene encoding an enzyme capable of converting a prodrug into a cytotoxic agent. Such molecular chimeras may be used to express enzymes of the invention in tumour cells in order to activate prodrugs. EP-A-415 731 describes incorporation of such molecular chimeras into viral vectors, e.g. adenoviral or retroviral vectors. Such viral vectors may also be adapted for utilization in the present invention.

Other recombinant viral vector delivery systems are described in WO91/02805, WO92/14829, WO93/10814, WO94/21792, WO95/07994, WO95/14091 and WO96/22277, the disclosures of which are incorporated herein by reference. Methods for producing vector delivery systems based on the above-mentioned disclosures may be used to deliver vectors encoding the activating enzyme to target cells.

Englehardt et al (Nature Genetics (1993) 4; 27–34) describes the use of adenovirus based vectors in the delivery of the cystic fibrosis transmembrane conductance product (CFTR) into cells, and such adenovirus based vectors may also be used in accordance with the present invention. Vectors utilising adenovirus promoter and other control sequences may be of use in delivering a system according to the invention to cells in the lung, and hence useful in treating lung tumours.

Vectors encoding the CPG2 carboxypeptidase may be made using recombinant DNA techniques known per se in the art. The sequences encoding the enzyme may be constructed by splicing synthetic or recombinant nucleic acid sequences together, or modifying existing sequences by techniques such as site directed mutagenesis. Reference may be made to "Molecular Cloning" by Sambrook et al (1989, Cold Spring Harbor) for discussion of standard recombinant DNA techniques. In general, the vector may be any DNA or RNA vector used in GDEPT therapies.

The CPG2 carboxypeptidase will be expressed from the vector using a promoter capable of being expressed in the cell to which the vector is targeted. The promoter will be operably linked to the sequences encoding the enzyme and its associated sequences.

Suitable promoters include viral promoters such as mammalian retrovirus or DNA virus promoters, e.g. MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

The c-erbB2 proto-oncogene is expressed in breast tissues at low levels and in a tissue restricted manner. In some tumour states, however, the expression of this protein in increased, due to enhanced transcriptional activity. Notable examples of this are breast tissue (about 30% of tumours), ovarian (about 20%) and pancreatic tumours (about 50–75%). In such tumours where expression of c-erbB2 is increased due to enhanced transcription or translation, the c-erbB2 promoter may be used to direct expression of the activating enzyme in a cell specific manner. The specificity of GDEPT may be increased since transfection of normal cells by a vector with a c-erbB2 promoter will provide only very limited amount of enzyme or none and thus limited activation of prodrug. The use of the c-erbB2 promoter and homologous promoters in GDEPT is more fully described in WO96/03151.

The prodrug for use in the system will be selected to be compatible with the CPG2 carboxypeptidase such that the enzyme will be capable of converting the prodrug to the active drug. Desirably, the toxicity of the prodrug to the patient being treated will be at least one order of magnitude less toxic to the patient than the active drug. Preferably the active drug will be several, e.g. 2, 3 or 4 or more orders of magnitude more toxic than the prodrug. Nitrogen mustard prodrugs are preferred. Other suitable prodrugs include those disclosed in WO96/03515.

Nitrogen mustard prodrugs include compounds of the formula:

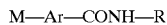

where Ar represents an optionally substituted aromatic ring system, R—NH is the residue of an α-amino acid R—NH$_2$ or oligopeptide R—NH$_2$ and contains at lease one carboxylic acid group, and M represents a nitrogen mustard group. The residue of the amino acid R—NH is preferably the residue of glutamic acid. It is disclosed in WO88/07378 that the enzyme carboxypeptidase G2 is capable of removing the glutamic acid moiety from compounds of the type shown above, and the removal of the glutamic acid moiety results in the production of an active nitrogen mustard drug. Prodrugs of a similar structure are also disclosed in WO94/02450, the disclosure of which is incorporated herein by reference.

In a further aspect, the present invention provides a pharmaceutical composition, medicament, drug or other composition comprising an enzyme of the invention. The composition may include a pharmaceutically acceptable carrier or diluent.

The invention also provides a kit comprising:
(a) a prodrug which can be converted to a cytotoxic drug by CPG2; and one of
(b(i)) an immunoglobulin/enzyme fusion protein or conjugate in which the immunoglobulin is specific for a cellular (e.g. tumour-associated) antigen and the enzyme is a carboxypeptidase enzyme;
(b(ii)) a ligand-enzyme conjugate or fusion protein, the ligand being specific for a cellular (e.g. tumour associated antigen) and the enzyme is a carboxypeptidase enzyme;
(b(iii)) a vector which encodes a carboxypeptidase enzyme which can be expressed in a cell (e.g. tumour cell) the carboxypeptidase being a carboxypeptidase of the invention.

In the kits of the invention, the vectors conjugates or fusion proteins may themselves be provided in a composition including a pharmaceutically acceptable carrier or diluent.

Compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise mature of the carrier or other material will depend on the route of administration, which may be oral, or by injection, e.g. cutaneous, subcutaneous or intravenous.

Administration of the prodrug and/or vector and/or fusion and/or conjugate is preferably in a "therapeutically effective amount", that being sufficient to show benefit to the patient. The doses of each component and the route and time-course of their administration will ultimately be at the discretion of the physician, who will take into account such factors as the nature and severity of what is being treated and the age, weight and condition of the patient.

Suitable doses of prodrug and conjugate for the ADEPT approach are given in Bagshawe et al. Antibody, Immunoconjugates, and Radiopharmaceuticals (1991), 4, 915–922. A suitable dose of conjugate may be from 2000 to 200,000 enzyme units/m$^2$ (e.g. 20,000 enzyme units/m$^2$) and a suitable dose of prodrug may be from 20 to 2000 mg/m$^2$ (e.g. 200 mg/m$^2$).

In order to secure maximum concentration of the fusion protein or conjugate at the site of desired treatment, it is normally desirable to space apart administration of the two components by at least 4 hours. The exact regime will be influenced by various factors including the nature of the tumour to be targeted and the exact nature of the prodrug. A typical regime is to administer the conjugate at 0 h, galactosylated clearing antibody at 24 h, and prodrug at 48 h. If no clearing antibody is used, it would generally be longer than 48 h before the prodrug could be injected.

In using the LIDEPT systems of the present invention the prodrug will usually be administered following administration of the ligand-enzyme fusion protein or conjugate. Typically, the ligand/enzyme will be administered to the patient, and its uptake monitored, for example by recovery and analysis of a biopsy sample of targeted tissue or by injecting trace-labelled protein ligand enzyme.

In using the GDEPT system the prodrug may be administered following administration of the vector encoding the activating enzyme. Typically, the vector will be administered to the patient and then the uptake of the vector by transfected or infected (in the case of viral vectors) cells monitored, for example by recovery and analysis of a biopsy sample of targeted tissue.

The amount of vector delivered will be such as to provide an effective cellular concentration of enzyme so that the prodrug may be activated in sufficient concentration at the site of a tumour to achieve a therapeutic effect, e.g. reduction in the tumour size. This may be determined by clinical trials which involve administering a range of trial doses to a patient and measuring the degree of infection or transfection of a target cell or tumour. The amount of prodrug required will be similar to or greater than that for ADEPT systems of the type mentioned above.

A treatment according to the present invention may be administered alone or in combination with other treatments, either simultaneously or sequentially dependent upon the condition to be treated.

In one aspect, the finding of immunogenic "hot-spots" provides a novel therapeutic method wherein a patient is administered different forms of CPG2 of the invention in successive rounds of therapy, such that any antibody response to a first modified CPG2 of the invention is not provoked by a second, different CPG2 of the invention which is administered in a second (or subsequent) round of therapy. Furthermore, a patient may be administered a wild-type form of CPG2 of the invention in a first round of therapy, followed after the first round (which may be more than one dose of wild-type CPG2) with a CPG2 of the present invention.

EXAMPLES OF THE INVENTION

Example 1

Identification and Modification of Immunogenic Epitopes

As described below, from a filamentous phage library of antibody genes obtained from CPG2 immunized mice we isolated two single chain Fv antibody fragments (CM79 and CM12) that partially blocked the polyclonal antibody response generated in patients who received CPG2 in ADEPT therapy. Using specialized metal chips coated with CM79/CM12 followed by antigen binding, selective proteolysis and surface enhanced laser desorption ionization affinity mass spectrometry (SELDI-AMS) the immunogenic region of CPG2 was characterised as incorporating the C-terminus and three loops from sequentially remote sequences which bound to both CM79 (C-terminus and one loop) and CM12 (three loops). (From these results, the immunogenic regions corresponding to SEQ ID NOS: 1,2, 3,4 were derived. We confirmed and silenced the epitopes corresponding to SEQ ID NO:2 and SEQ ID NO:4 by mutagenesis to give CPG2 variants with negligible binding to CM79. The variants showed significant reduction in reactivity against sera from patients with post-therapy immune responses to wild-type CPG2.

1.1 Characterization of the Anti-CPG2 Antibody Phage Library

An anti-CPG2 antibody library was generated containing $1.78 \times 10^7$ sFv clones. The twelve sFv clones which gave the highest optical density (OD) readings in ELISA with CPG-coated plates were chosen. These were then tested by serum inhibition ELISA for their ability to block the human polyclonal antibody response made by 2 patients who had received wild-type CPG2 in ADEPT clinical trials. Results showed a range of 0%–20% inhibition of patients' sera binding by the sFvs. The strongest inhibitors, clones CM79 and CM12, were sub-cloned and purified to allow detailed analysis. CM79-saturated CPG2 was presented to sera from 10 CPG2-immunized patients and reductions of up to 18% of the IgG response were observed (FIG. 1). Although the examples below describe in detail the procedures related to CM79 used to identify epitopes SEQ ID NO:2 and SEQ ID NO:4, it should be understood that similar procedures were carried out starting with clone CM12 resulting in identification of epitopes SEQ ID NO:1 and SEQ ID NO:3. The epitope corresponding to SEQ ID NO:5 was identified by molecular dynamics modelling as described below.

1.2 Epitope Identification

Epitopes were identified using SELDI-AMS epitope mapping and prediction of surface exposed regions.

i) SELDI-AMS

CM79 was subcloned into a pUC119 hexahistidine-tag vector, expressed and IMAC purified (Casey, J. L. et al. *J. Immunol. Methods* 179, 105–116 (1995)). CM79 mass was determined using SELDI-AMS. To an NP1 SELDI chip (Ciphergen Biosystems Plc, Ca., USA) 1 ml of CM79 (0.5 mg/ml in distilled water) was added with sinapinic acid matrix (5 mg/ml in 50% acetonitrile, 0.5% trifluoracetic acid). A PBS-1 mass spectrometer (Ciphergen Biosystems Plc.) was used to collect mass data. The laser intensity was 20 with 100 shots collected and averaged per sample. For SELDI-AMS epitope mapping, all incubation stages were 1 h, room temperature, in a humidity chamber unless stated otherwise. 2 ml of CM79-His or anti-CEA sFv M009-His (both 0.3 mg/ml), were incubated on a PS1 SELDI chip (Ciphergen Biosystems Plc.). 4 ml of 1 M ethanolamine (pH 8) was added to each spot and incubated for 20 min. The chip was washed with 4×5 µl of PBS+0.1% Triton X-100 (PBST) and submerged in PBST for 15 min.

Antigens (1 ml of 3 mM CPG2+10 mM BSA, or 10 mM BSA) were incubated on the chip. The chips were washed and incubated with Glu-C protease (Boehringer-Mannheim-Roche, UK). Enzyme to substrate ratios were 1:20 or 1:50 diluted in PBST. Protease digestions were performed for 1.5 h. Matrix was 0.5 µl α-cyano-4-hydroxycinnamic acid (CHCA) at 5 mg/ml in 50% acetonitrile/0.1% trifluoroacetic acid. Mass data was acquired using the PBS-1 mass spectrometer, 100 samples per spot with laser intensity setting at 10 were collected and averaged in automatic mode. Calibration was external using bovine ubiquitin (8564.8 Da).

ii) Predicting Surface Exposed Regions

Figure 3A:
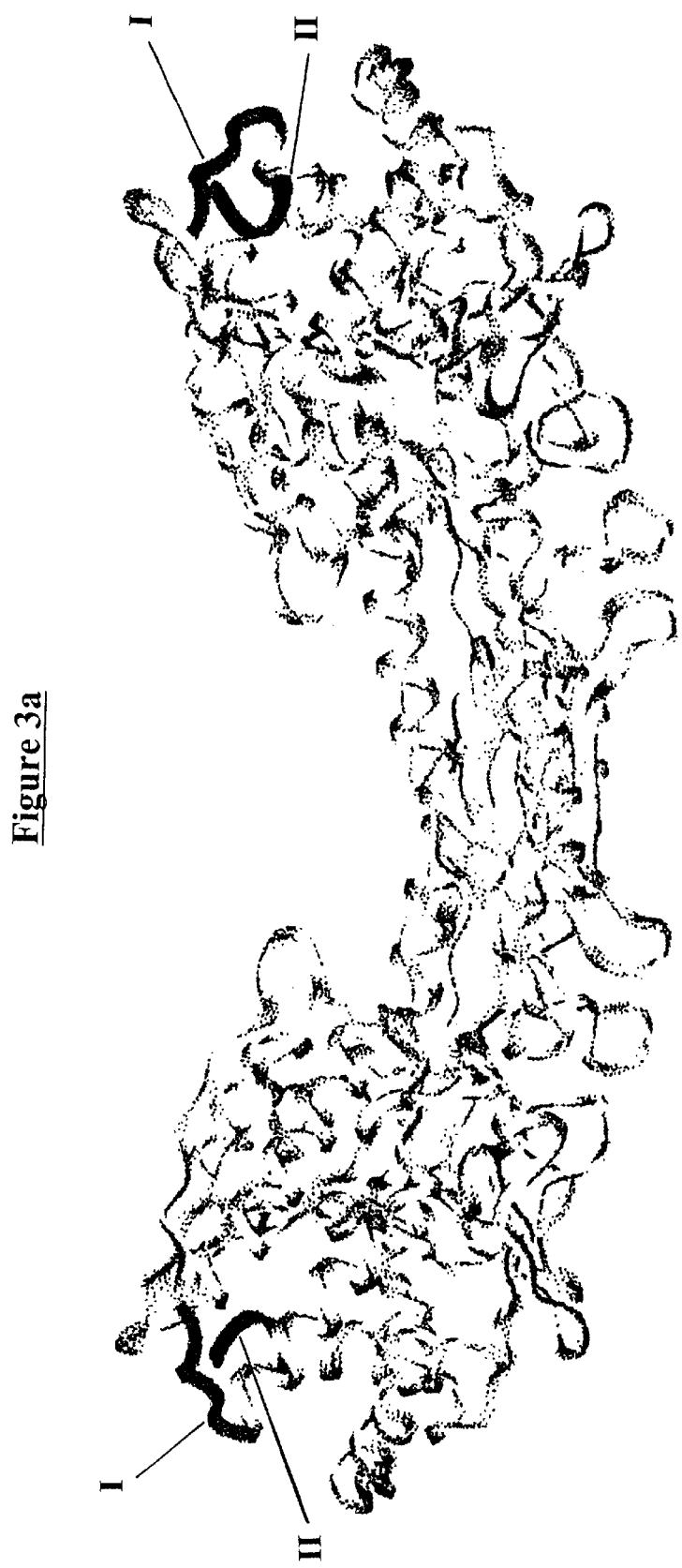
FIG. 3A shows a representation of the X-ray crystal derived structure of CPG2, showing regions I and II.

Surface exposed regions of Glu-C digested CPG2 peptides were determined using the X-ray crystal determined structure of CPG2 (Swiss-Prot. Pdb reference 1CG2), Insight II (MSI, UK) and the DSSP solvent accessibility algorithm (Rowsell, S. et al. *Structure* 5, 337–347 (1997)). Glu-C generated fragments of CPG2 were identified on the Protein Analysis Worksheet (PAWS) (ProteoMetrics, USA). Analysis of the CPG2 crystal derived conformational structure (Rowsell, S. et al. *Structure* 5, 337–347 (1997)) showed that peptide Y[159–176]E was solvent exposed (Kabsch, W. & Sander, C. *Biopolymers* 22, 2577–2637 (1983))(solvent exposure>78%) about residues Y[159–163]D, which we termed Region I, shown in FIG. 3a. Peptide Y[391–415]K was solvent exposed about residues 413–414, this was termed Region II (FIG. 3A). These solvent exposed regions are only 6 Å apart between Asp163 of Region I and Ala413 of Region II. The close spatial proximity of the two surface exposed regions supported their role as the CM79 binding epitope. Molecular dynamics modelling confirmed these results and moreover suggested that, with respect to region I (residues 159–163), residues 157 and 158 are also surface exposed and therefore form part of the epitope. Similarly, molecular dynamics modelling suggested that in addition to residues 413 and 414 of region II, residues 412 and 415 are also surface exposed and so may form part of the epitope. Indeed, as described below and as shown in Table 1, substitution of an alanine residue at residue 412 resulted in decreased CM79 binding. We hypothesized that if Regions I and II comprised a clinically relevant epitope that we had defined with CM79, then mutations of that epitope would reduce recognition by CM79 and patients' antibodies.

Figure 2:
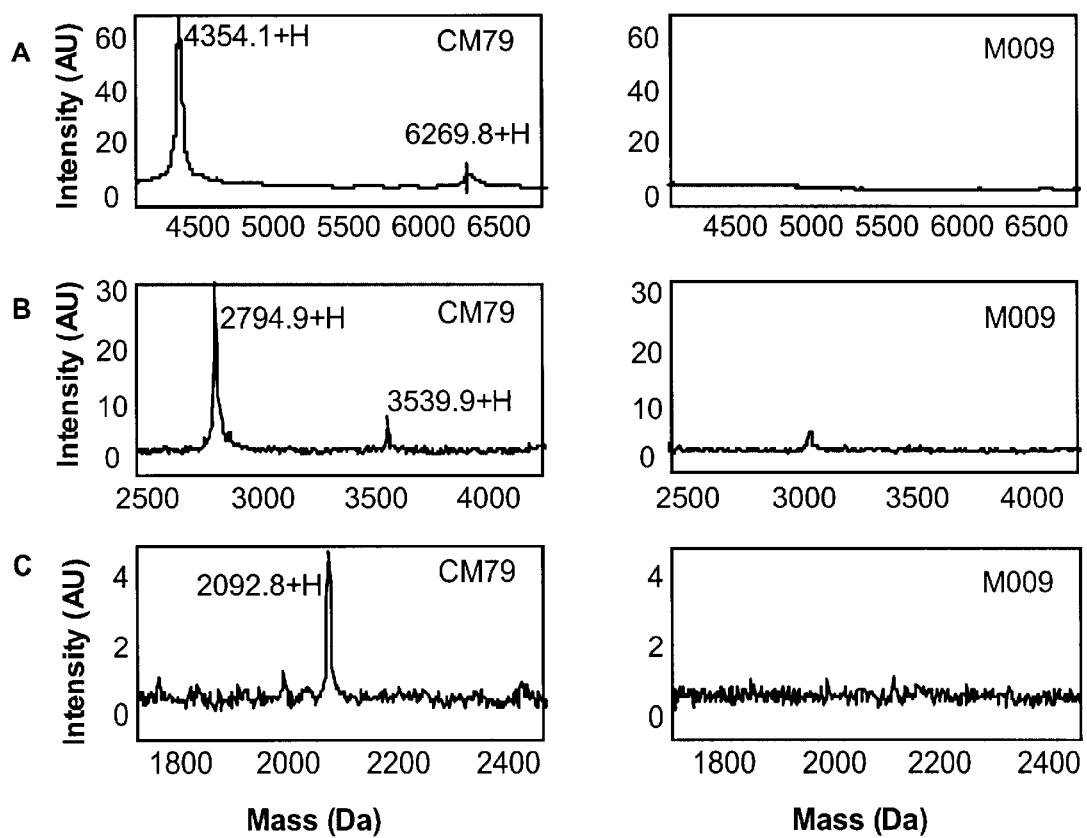
FIG. 2 illustrates three segments of the SELDI epitope mapping mass spectra of CPG2 with CM79 (left hand spectra) and with non-CPG2 binding sFv M009 controls (right hand spectra). 2A) Glu-C digested CPG2 peptides R[356–415]K (mass 6269.8 Da) and S[376–415]K (mass 4354.1 Da). 2B) Glu-C digested CPG2 peptides Y[391–415]K (mass 2794.9) and Y[159–189]E (mass 3539.9 Da). 2C) Glu-C digested CPG2 peptides Y[159–176]E (mass 2092.8 Da)

SELDI-AMS combined with Glu-C proteolytic epitope mapping of the CPG2/CM79 complex identified five CM79 binding peptides derived from CPG2 (FIG. 2). CPG2 fragments identified were numbered according to the CPG2 Swiss-Prot entry (accession code P06621) (FIG. 3b). The observed peptide masses were, 6269.8+H Da assigned to CPG2 R[356–415]K mass 6270.2 Da (nearest alternative A[314–375]E mass 6281.1 Da) (FIG. 2A), 4354.1+H Da assigned to CPG2 S[376–415]K mass 4354.1 Da (nearest alternative A[314–356]E mass 4365.0 Da) (FIG. 2A), 2794.9+H Da assigned to CPG2 Y[391–415]K mass 2794.4 Da (nearest alternative A[347–375]E mass 2748.0 Da) (FIG. 2B), 3539.9+H assigned to CPG2 Y[159–189]E mass 3539.8 Da (nearest alternative K[208–243]E mass 3537,0 Da) (FIG. 2B), and 2092.8+H Da assigned to CPG2 Y[159–176]E mass 2092.2 Da (nearest alternative E[355–375]E mass 2063.2 Da) (FIG. 2C). The proteolytic fragments were all derived from two sequentially remote regions of CPG2. These results were obtained in duplicate on each assay chip and on subsequent repetitions of the experiment. Control spectra (right side of FIG. 2) were performed using non-CPG2 binding sFv M009.

1.3 Generation of MFE-23::CPG2-his Variants

MFE-23, a recombinant scFv produced by filamentous phage technology, has shown good localisation to CEA-producing tumours in patients. MFE-23 is well characterised, is produced in high yields and has high affinity and specificity for CEA. A radiolabeled fusion protein of MFE-23::CPG2 expressed in *E.coli* has been shown to localise to colorectal tumour xenografts in nude mice(Bhatia et al, Int. J. Cancer 85 571–577, 2000).

MFE-23::CPG2 Fusion proteins were produced with variant CPG2. Changes to (KEYGVRD)(SEQ ID NO:2) were made by insertion of annealed pairs of oligonucleotides encoding the substituted amino acids into HindIII and KpnI cohesive termini previously created by PCR mutagenesis (Purdy, D. et al. *J. Medical Microbiol.* 49,473–479 (1999)) to flank Region I in wild type (wt) CPG2 plasmid. Changes to(GAGK)(SEQ ID NO:4) were also prepared. Eight variants are illustrated in Table 1 and are labelled as V1 to V6.

Figure 4:
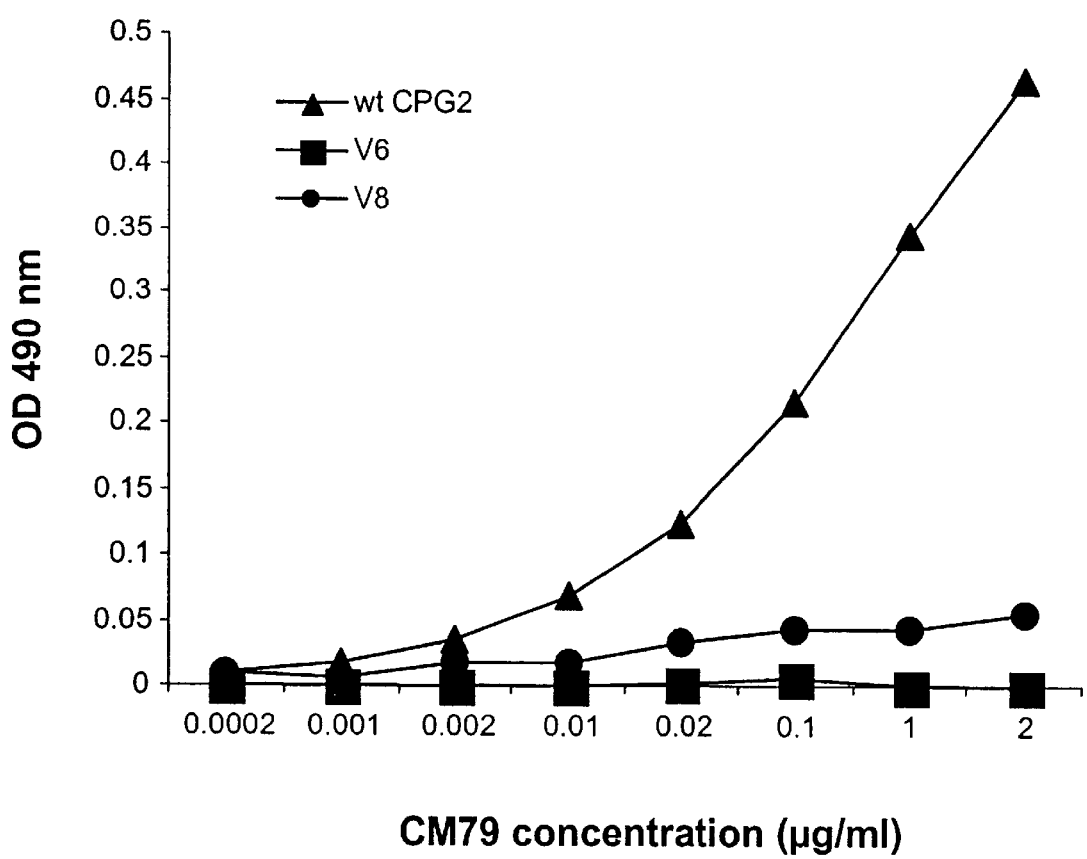
FIG. 4 illustrates CM 79 binding to wt CPG2, variant V6 and variant V8, determined by ELISA.

CM79 binding and CPG2 enzyme activity of all CPG2 variants were initially tested in clarified culture supernatants for CM79 binding. The results, shown in Table 1, demonstrate that Arg162 was critical for CM79 binding (sFv binding to V6 was up to 99% less than binding to wt MFE-23::CPG2, FIG. 4(wt=wild-type)). The variant V8 MFE-23::CPG2 indicated the role of the c-terminus in CM79 binding of CPG2 (FIG. 4, Table 1). CM79 bound to all the remaining CPG2 variants (Table 1).

TABLE 1

CPG2 variants tested for CM79 binding and enzyme activity. A single mutation was made in each variant (bold) in either the KEYGVRD (SEQ ID NO:2) or the GAGK (SEQ ID NO:4) regions. Wild-type MFE-23::CPG2 and variant V6 were CEA affinity chromatography and FPLC purified for CM79 binding, serum binding and enzyme activity assays.

| | Conformational epitope | | | |
|---|---|---|---|---|
| Clone | Region 1 | Region 2 (C-term.) | Enzyme Activity | CM79 binding |
| wild-type CPG2 | KEYGVRD (SEQ ID NO:2) | GAGK (SEQ ID NO:4) | Yes | Yes |
| V1 | AEYGVRD (SEQ ID NO:14) | GAGK (SEQ ID NO:4) | Yes | Yes |
| V2 | KAYGVRD (SEQ ID NO:15) | GAGK (SEQ ID NO:4) | Yes | Yes |
| V3 | KEAGVRD (SEQ ID NO:16) | GAGK (SEQ ID NO:4) | Yes | Yes |
| V4 | KEYAVRD (SEQ ID NO:17) | GAGK (SEQ ID NO:4) | Yes | Yes |
| V5 | KEYGARD (SEQ ID NO:18) | GAGK (SEQ ID NO:4) | Yes | Yes |
| V6 | KEYGVAD (SEQ ID NO:19) | GAGK (SEQ ID NO:4) | Yes | Reduced (up to 99%) |
| V7 | KEYGVRA (SEQ ID NO:20) | GAGK (SEQ ID NO:4) | None | Yes |
| V8 | KEYGVRD (SEQ ID NO:2) | AAGK (SEQ ID NO:21) | Yes | Reduced (up to 89%) |

1.4 ADEPT Patient Sera Binding to Variant V6 and Wild-Type (wt) CPG2

As variant V6 was shown to have negligible binding to CM79 it was selected for testing for reactivity with patient sera.

V6 and wild-type (wt) MFE-23::CPG2 were expressed and purified from 6×250 ml culture volumes. Protein yields were 1.3 mg/l for V6 and 0.84 mg/l for wt MFE-23::CPG2. Both proteins were radiolabelled using the chloramine-T method (Greenwood, F. C. & Hunter, W. M. *Biochem. J.* 89, 116–123 (1963)). with 37 MBq iodine-125 sodium iodide added to 1 ml of 0.5 mg/ml protein. Radiolabelled proteins were FPLC purified using a Superose 12 column (Pharmacia; PBS mobile phase 0.5 ml/min). Gamma radiation emitting fractions at 135 kDa elution point were tested for CPG2 enzyme activity. Protein concentrations were determined using Lowry reagent according to the manufacturer's protocol (BioRad).

V6 was presented to 15 serum samples from patients who had antibodies to CPG2 as a result of receiving ADEPT. 2% BSA blocking, wash and O-phenylenediamine dihydrochloride (Sigma) detection stages were as described by Bhatia et al(Int. J. Cancer 85 571–577, 2000). ELISA plates (Maxisorb, Nalgene-Nunc International, UK) were coated overnight at 4° C. with 0.5 mg CPG2, 0.02 mg V6 or 0.02 mg wt MFE-23::CPG2 per well. Library derived sFv binding to CPG2 was detected with mouse anti-myc tag antibody 9E10, followed by sheep anti-mouse IgG peroxidase conjugated antibody (SAM-HRP) (Amersham Life Sciences, UK). To monitor CM79-His binding to CPG2 or the MFE-23::CPG2 variants CM79 was detected using mouse anti-His tag antibody (Dianova, Germany), followed by SAM-HRP. The patient serum inhibition assays were performed by saturating CPG2 coated wells with CM79 at 25 mg/ml. ADEPT patient serum binding to CPG2 or the MFE-23::CPG2 variants was detected with goat anti-human IgG HRP (Sigma).

Figure 5:
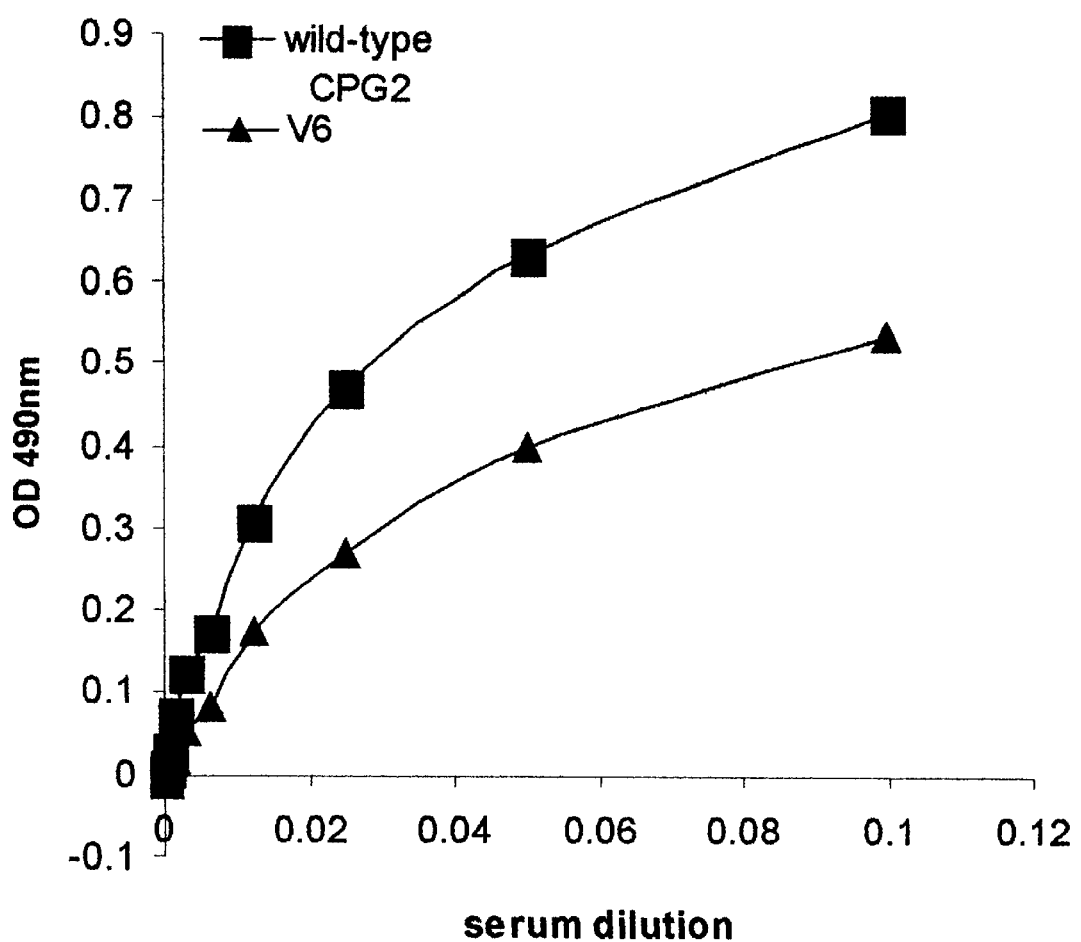
FIG. 5 illustrates an example of patient serum (A21) binding to wt CPG2 and variant V6. Binding was determined by ELISA. (Serum dilution 0.1=a 1 in 10 fold dilution.

Results showed that all these sera had lower binding to V6 than the wt MFE-23::CPG2 (FIG. 5, Table 2). Extrapolating the maximum ELISA optical density signal for undiluted serum, the antibody binding reductions in the patient group had the range 10.2–65.3%, with a median reduction of 45.1% . Rabbit anti-MFE-23 serum was used to detect the MFE-23 domains of wt and V6 fusion proteins. As each CPG2 variant is linked to an MFE-23 sFv, equimolar concentrations of the fusion proteins should have equivalent anti-MFE-23 responses. The anti-MFE-23 binding responses for the two fusion proteins varied by only 5.8%, a difference within the limits of ELISA experimental error.

TABLE 2

Percentage reduction of 15 ADEPT patient sera binding to V6 compared to wt MFE-23::CPG2 determined by ELISA. Rabbit anti-MFE serum is directed against the antibody domain of the fusion proteins and acts as a negative control.

| Serum | Decrease in antibody binding (%) |
|---|---|
| A1 | 30.1 |
| A3 | 65.3 |
| A4 | 13.3 |
| A8 | 45.1 |
| A11 | 62.0 |
| A12 | 48.7 |
| A13 | 57.6 |
| A14 | 56.0 |
| A15 | 25.5 |
| A16 | 56.7 |
| A17 | 20.1 |
| A18 | 10.2 |
| A19 | 51.5 |
| A20 | 14.9 |
| A21 | 30.2 |
| Rabbit anti-MFE | 5.8 |

Example 2

Glycosylation of CPG Improves Retention of Fusion Proteins in Tumours Despite Rapid Clearance From Normal Tumours Although radiolabeled fusion protein of MFE-23::CPG2 expressed in *E.coli* has been shown to be promising candidate for ADEPT if favorable enzyme delivery is established (Bhatia et al, Int. J. Cancer 85 571–577, 2000), the yields obtained with this bacterially expressed product were too low for developing a clinical product. Therefore, the present inventors have investigated expression in yeast *Pichia pastoris*. The *Pichia pastoris* expressed product was constructed with tags for identification and expression. Experiments performed with the *Pichia pastoris* expressed fusion proteins led to two unexpected findings:

a) that the glycosylated fusion proteins were retained in active form in the tumour, despite rapid clearance from normal tissues (described in the present Example);and b) that the presence of C-terminal tags reduced immunogenicity in animal models (described in Example 3).

2.1 Glycosylation

Oligosaccharides were identified by collision induced disassociation mass spectrometry (CID) of trypsinated fragments of MFE-23::CPG2 gly-his (*Pichia pastoris* expressed MFE-23::CPG2 fusion protein with a C-terminal hexahistidine tag)

There are three potential N-glycosylation sites on CPG2, CID showed that only two of the three sites are glycosylated by *Pichia pastoris*.Asn 222-Glycosylated, mostly mannose 5–13 chains Asn 264—Not glycosylated (not solvent exposed) Asn 272—Glycosylated, mostly mannose 8–10 chains Some O-linked glycosylation (a maximum of five mannose) is present on the MFE moiety of MFE-23::CPG2gly-his.

2.2 Pharmacokinetics & Biodistribution of MFE::CPG2gly-his In Mice

Nude mice bearing LS174T xenografts were injected i.v. with the fusion protein (25 units per mouse). Blood samples were taken at different times after injection. Plasma and tissues were assayed for CPG2 activity as follows:—CPG2 activity in tumor and normal tissues was measured by in-vitro turnover of the substrate methotrexate (MTX) by localised enzyme and measurement of the metabolite peak by HPLC. Briefly. a calibration curve for each tissue was constructed by incubating the relevant tissue (taken from untreated mouse) with varying concentrations of CPG2 and a fixed concentration of methotrexate and analysing the solution by HPLC to give a standard line for CPG2 concentration v. metabolite peak area formed. Tissue homogenates were prepared in assay buffer (PBS+Zinc Chloride) w/v 20% and diluted further as appropriate and incubated with methotrexate. The reaction was stopped by addition of ice cold methanol (1:1). The supernatant was analysed by HPLC.

2.3 Clearance

Figure 6:
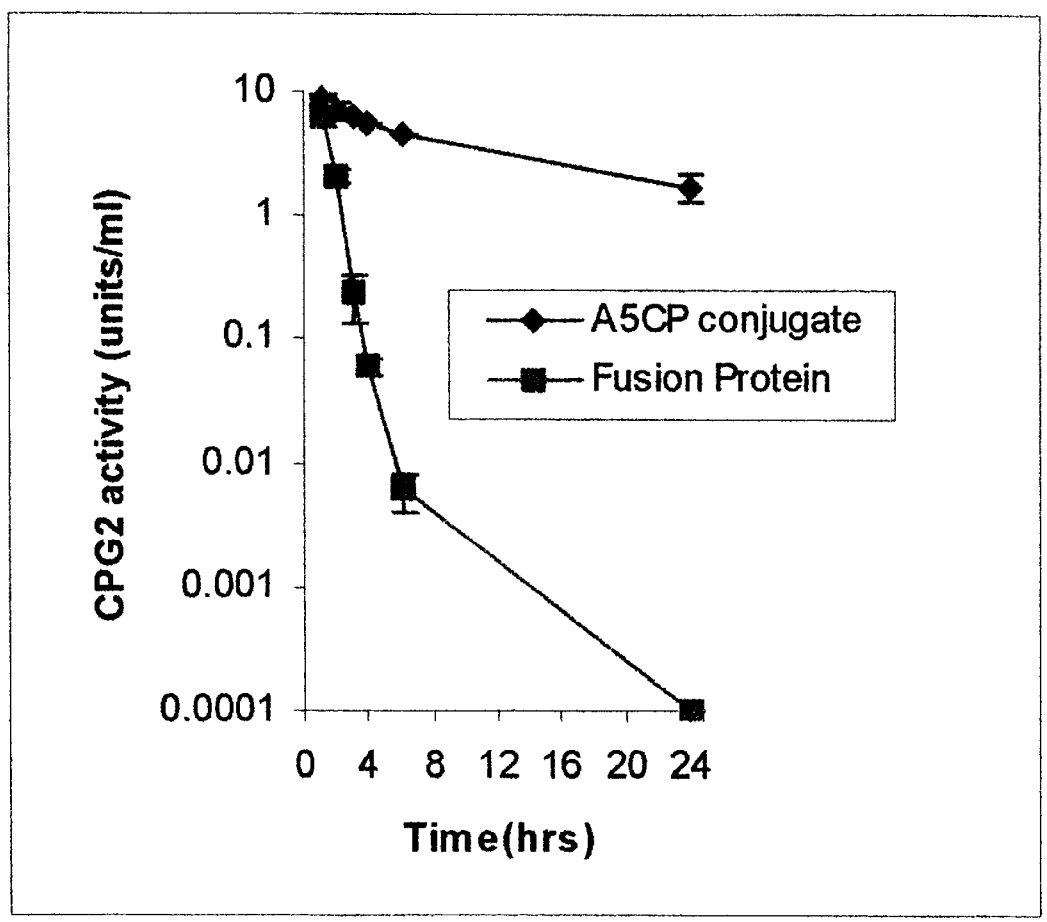
FIG. 6 illustrates plasma clearance of CPG2 activity in LS174T xenografted nude mice given MFE23::CPG-gly-his fusion protein.

Results for plasma clearance of MFE-CPG2gly-his in comparison to those obtained with a chemical conjugate of monoclonal anti-CEA with CPG2 (A5CP) are shown in FIG. 6. Rapid clearance of MFE::CPG2gly-his is demonstrated.

2.4 Biodistribution of MFE-CPG2gly-his

Figure 7:
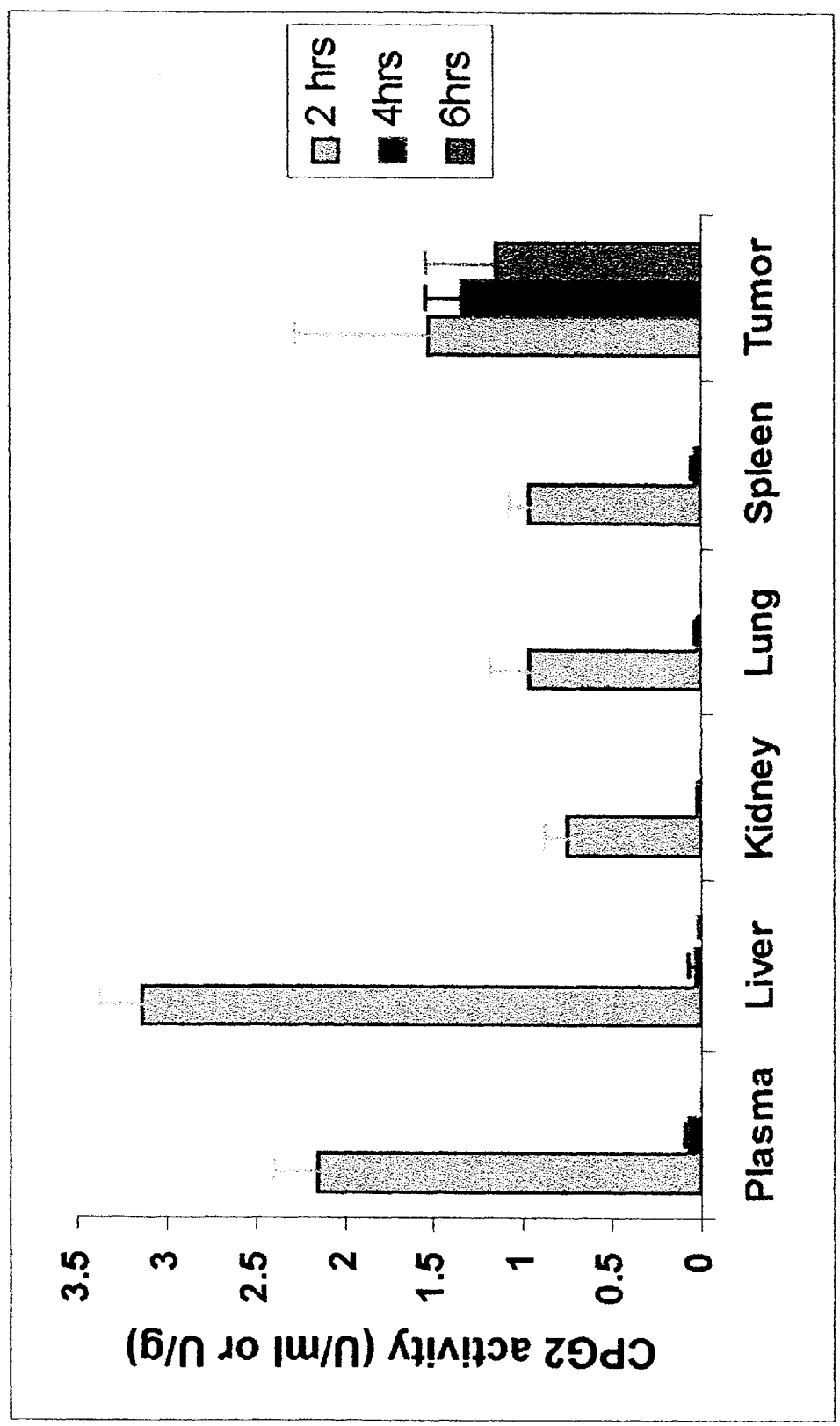
FIG. 7 illustrates biodistribution of CPG2 activity in LS174T xenografted nude mice given MFE23::CPG-gly-his fusion protein.
Figure 8:
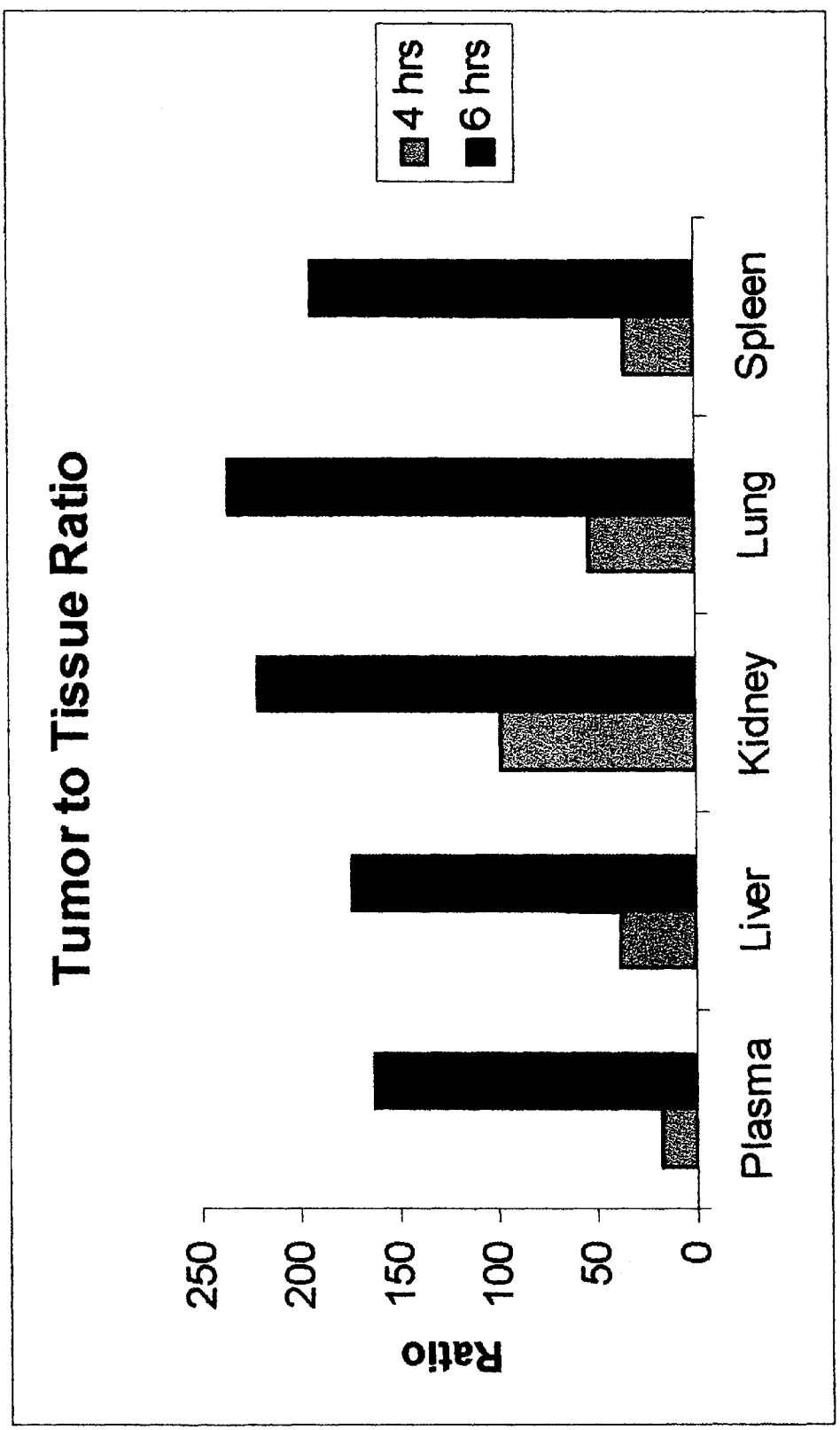
FIG. 8 illustrates tumour to normal tissue ratios in LS174T xenografted nude mice given MFE23::CPG-gly-his fusion protein.

To assess CPG2 activity in enzyme activity in LS174T xenografted nude mice, tumour, liver. kidney, lung and spleen were collected from 4 mice per time point at 2, 4 and 6 hours after intravenous injection of MFE-23::CPG2 gly-his fusion protein and enzyme activity was assayed in tissue extracts. Results, shown in FIG. 7, indicate that, despite rapid plasma clearance, enzyme activity persists in the tumours. In addition, selective localisation in the tumour occurs at much earlier time points than observed with the A5B7-F(ab')2-CPG2 conjugate. Rapid plasma clearance in conjunction with high levels of CPG2 activity retention in tumours resulted in tumour to plasma ratios of 163:1 at 6 hrs after fusion protein injection. Tumour to liver, kidney, lung and spleen ratios at 6 hrs post injection were 254, 245, 158 and 160 respectively(FIG. 8).

2.5 MFE-23::CPG2gly-his AND MFE-23::CPG2gly-myc-his Remain Intact in Tumour

In addition to HPLC analysis of CPG2 enzyme activity in excised tissue (FIG. 7), the integrity of the enzymatically active material was tested to demonstrate that enzyme activity was due to MFE-23::CPG2 which had remained intact in the tumour.

$^{125}$I radiolabelled MFE-23::CPG2gly-his or MFE-23::CPG2gly-myc-his was injected intravenously to nude mice bearing LS 174T human colorectal tumour xenografts. Four hours later, the mice were sacrificed and the tumours were removed, homogenised and subjected to SDS-PAGE. Radiolabelled material was visualised by autoradiography. This demonstrated that $^{125}$I-MFE-23::CPG2 gly in the tumour had the same molecular weight profile as $^{125}$I-MFE-23::CPG2 gly prior to injection, indicating stability in vivo.

2.6 Relative Stability in Vivo

Figure 9A:
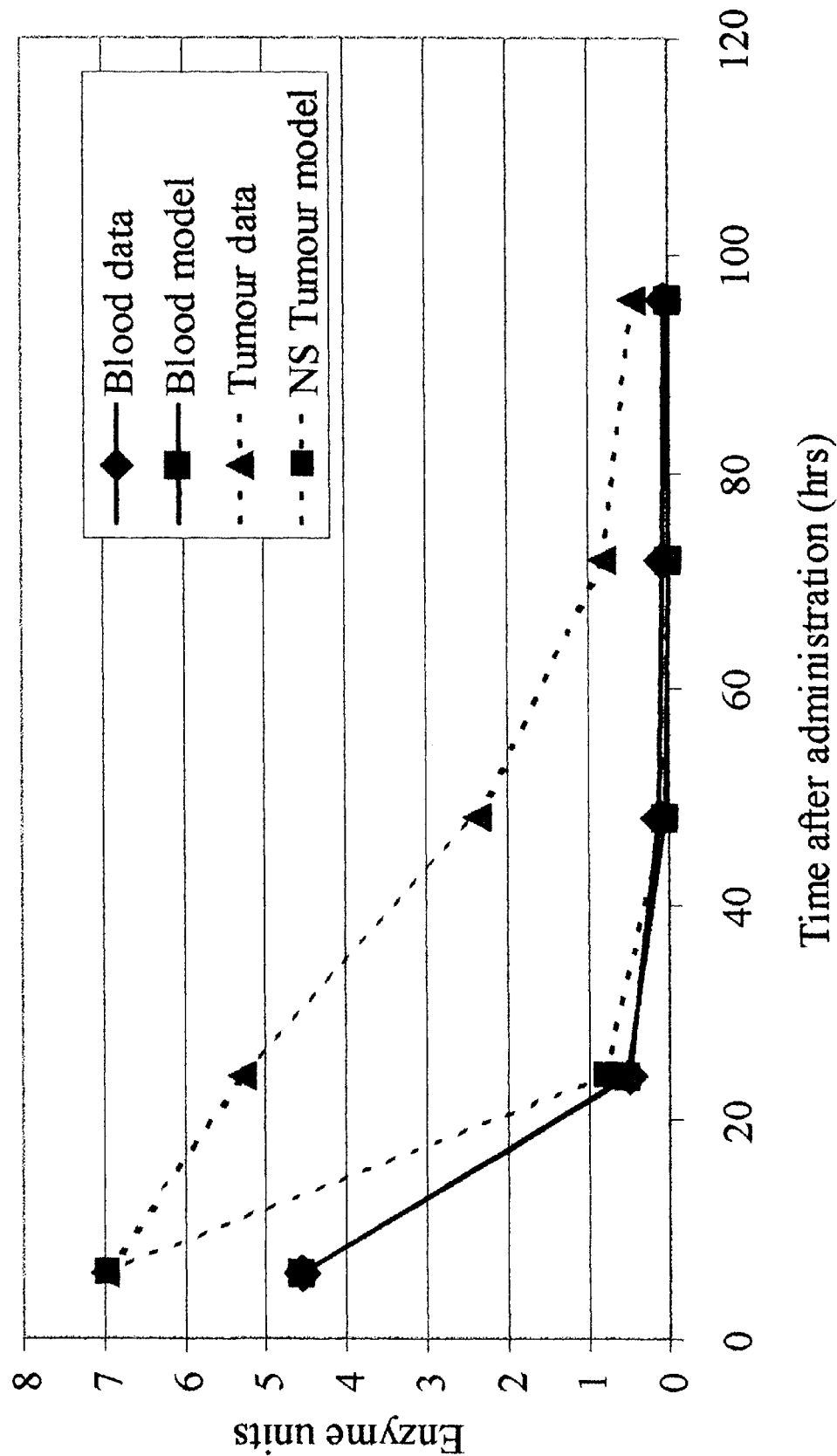
FIG. 9A illustrates time-activity curves for actual tumour and blood data for the glycosylated fusion protein along with the models that describe blood clearance and uptake of the non-specific (NS) antibody in tumour.
Figure 9B:
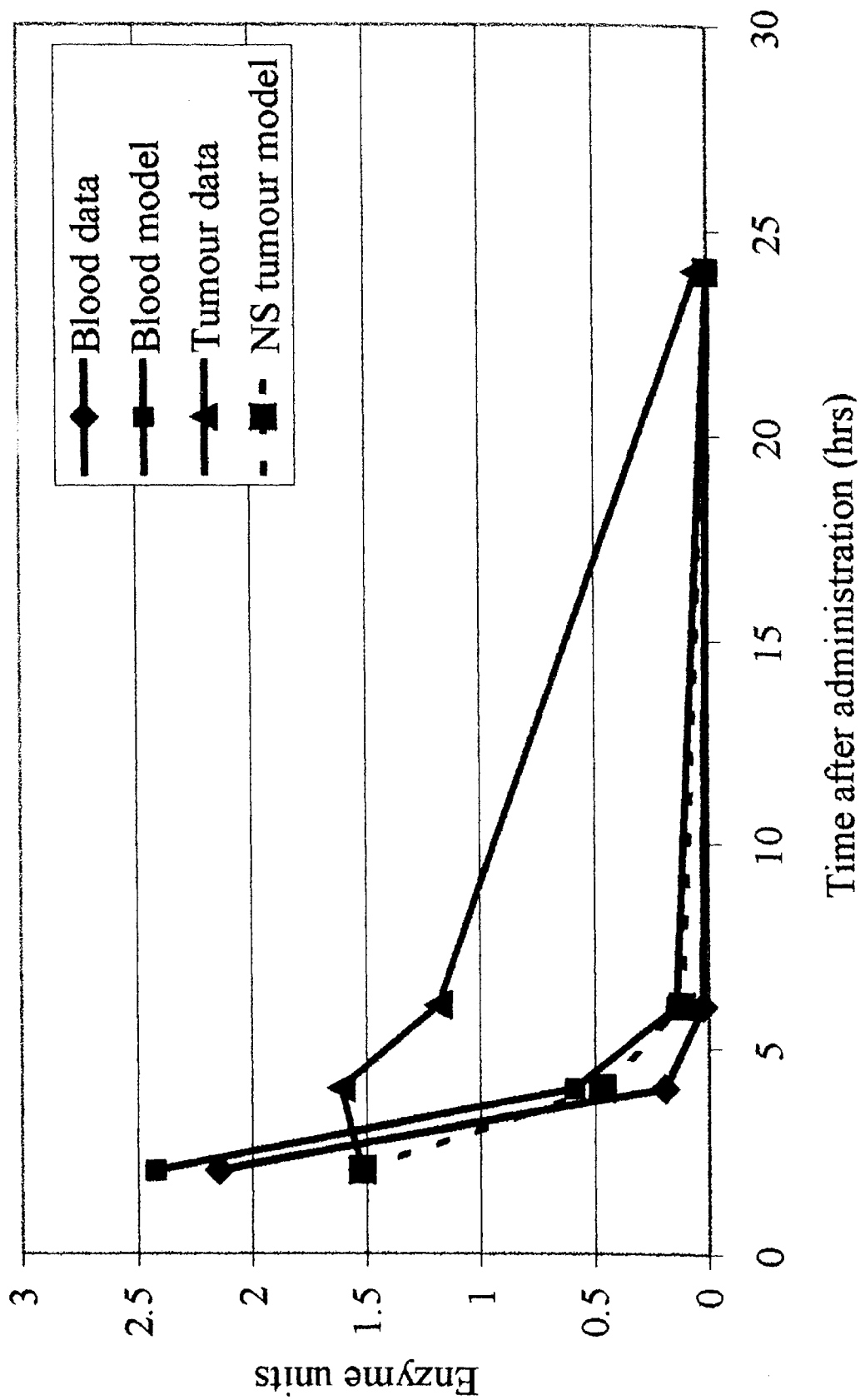
FIG. 9B illustrates time-activity curves for actual tumour and blood data for the non-glycosylated fusion protein along with the models that describe blood clearance and uptake of the non-specific (NS) antibody in tumour.
Figure 10A:
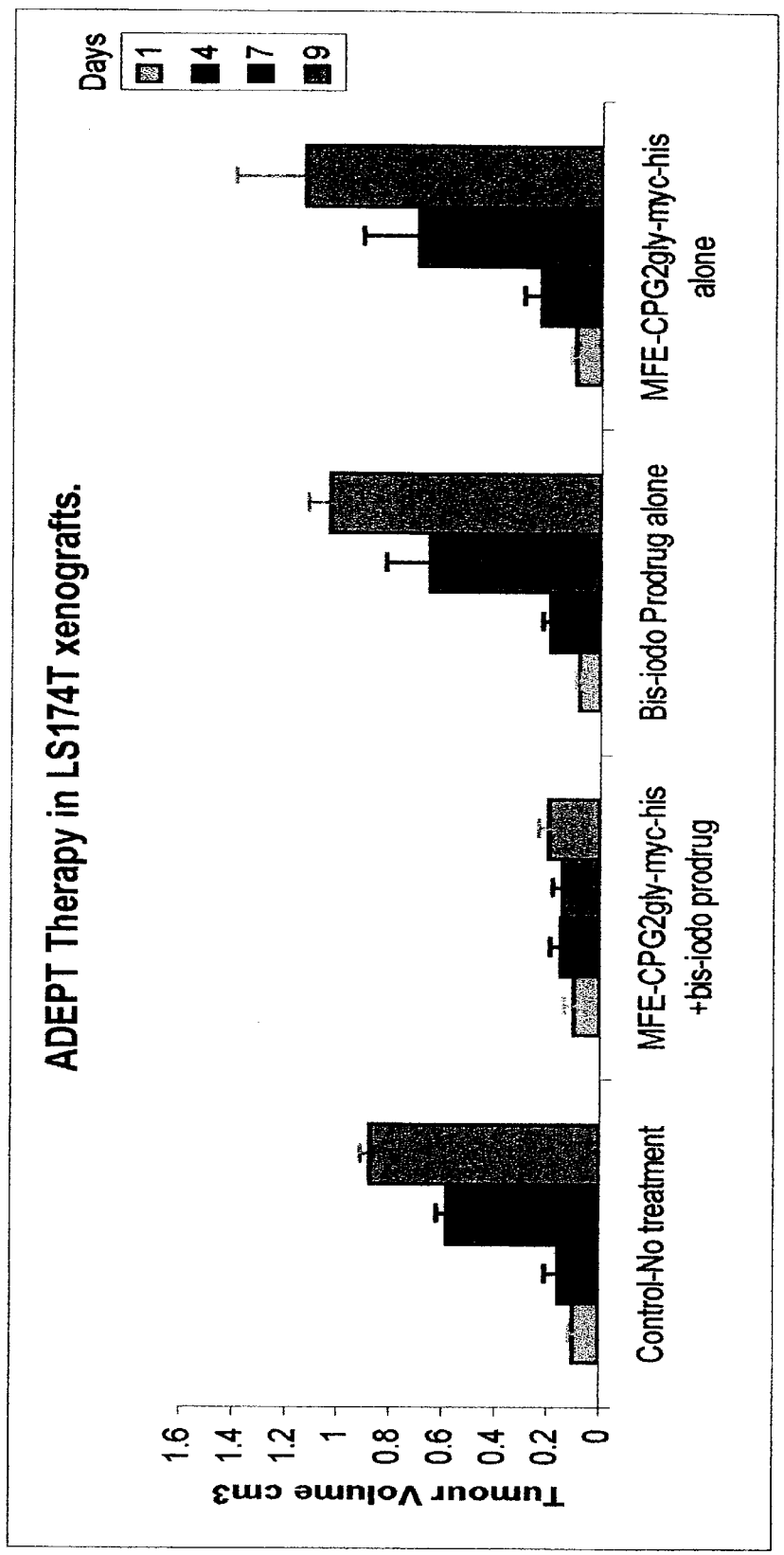
FIG. 10A illustrates the effect of ADEPT therapy in LS174T xenografted nude mice given MFE23::CPG-gly-myc-his fusion protein in combination with bis-iodo phenol mustard prodrug (ZD2767P).
Figure 10B:
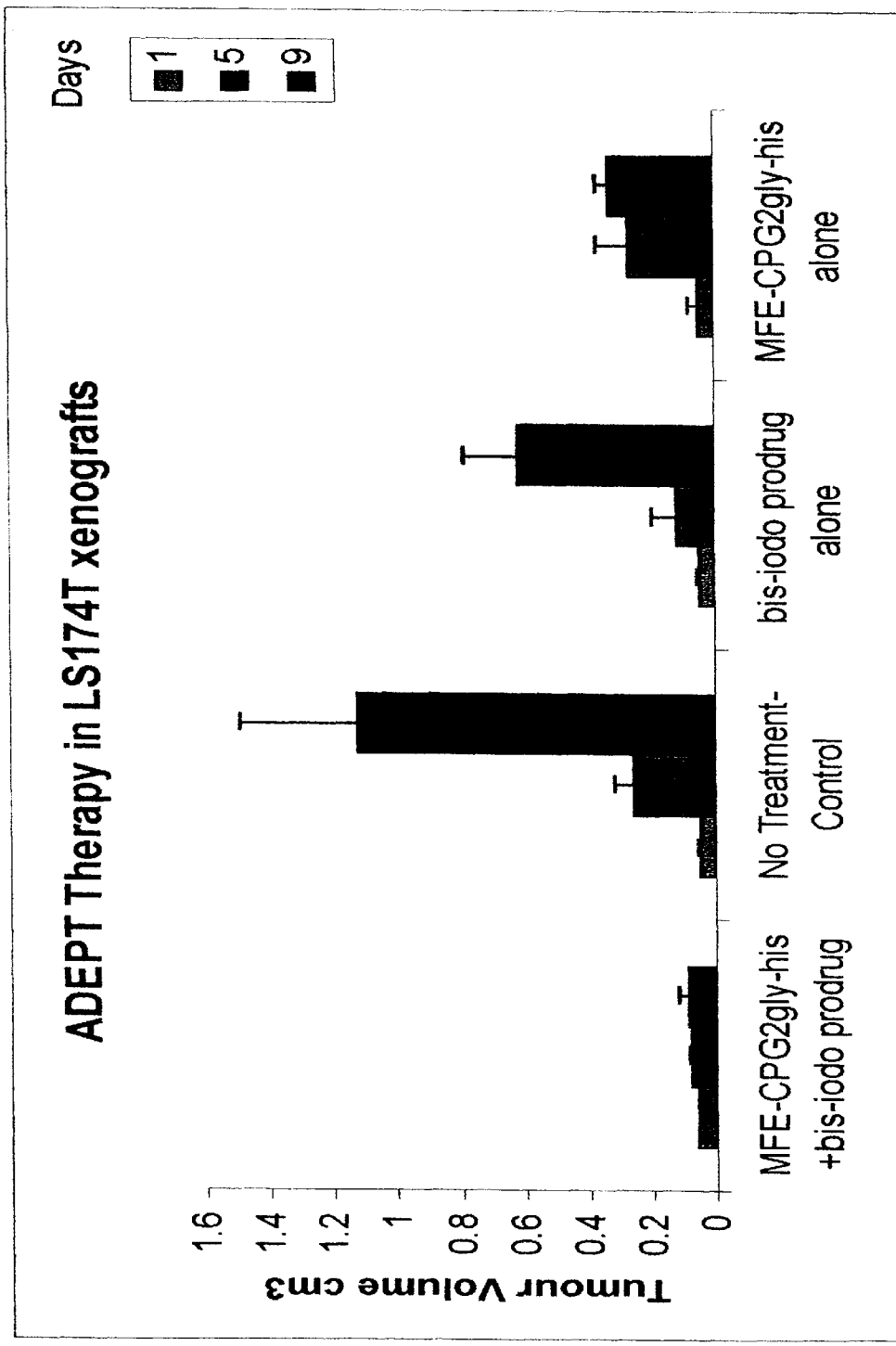
FIG. 10B illustrates the effect of ADEPT therapy in LS174T xenografted nude mice given MFE23::CPG-gly-his fusion protein in combination with bis-iodo phenol mustard prodrug (ZD2767P).

Effective targeted therapy relies on efficient antibody retention in tumour after clearance from normal tissue and is primarily influenced by the molecular size, stability and functional affinity of the antibody. Molecular size determines the circulating half-life of the antibody and, due to the dynamic recirculation between blood and tumour, ultimately controls the uptake and residence time in tumour. Large antibodies show better tumour uptake and can deliver prolonged therapy but are impractical due to their long circulating half-life. By contrast, small antibodies show the perfect clearance pattern but are not retained in tumour long enough to allow effective therapy. Ideally, the therapeutic window would be extended by improving stability and affinity. However, due to the obvious influence of molecular size it is difficult to assess the isolated role of stability and affinity on retention. One way of assessing retention, that is not related to molecular size is to compare the area under the time-uptake curve for the tumour-specific antibody with that of a nonspecific antibody that has the same characteristic clearance from blood. We have done this by fitting a bi-exponential function to the blood data from the specific antibody. This function may then be used along with a simple mathematical model, that assumes recirculation between blood and tumour is caused only by a concentration gradient between them, to simulate the equivalent time-uptake curve for a non-specific antibody. The area under each curve is obtained by integrating to infinity with respect to time and the retention may be assessed by ratio of this integral for the specific relative to the nonspecific antibody. This ratio is 64.5 for the glycosylated fusion protein (FIG. 9A) compared to only 4.4 for the non-glycosylated fusion protein (FIG. 9B). Therefore, we estimate a potential 15-fold increase in therapeutic efficacy with the glycosylated product. ps 2.7 Therapy Studies Show Efficacy With MFE-23::CPG2gly-his And MFE-23::CPG2gly-myc-his Fusion Proteins Mice were injected with fusion protein (25 units per mouse) i.v. when the tumours reached 0.1–0.2 $Cm^3$ and were in exponential growth. The prodrug was given X3 over 2 hrs between 4 and 6 hours after fusion protein injection at 90 mg/kg per mouse i. p. Different control groups included fusion protein alone (25 units/mouse ), prodrug alone (90 mg/kg X3) and a no treatment control group. Tumours were measured on day one prior to treatment and subsequently on $3^{rd}$ or $4^{th}$ day until tumour volume reached 2 $cm^3$. The measurements were carried out in three dimensions (length, width and height) and the tumour volume estimated as length×width×height divided by 2. The mean tumour volume (+/−sem) is plotted against days after i; treatment. The fusion proteins in combination with bis-iodo prodrug showed good growth delay of the tumour (see FIGS. 10A & 10B).

2.8 Toxicity Studies

Figure 11A:
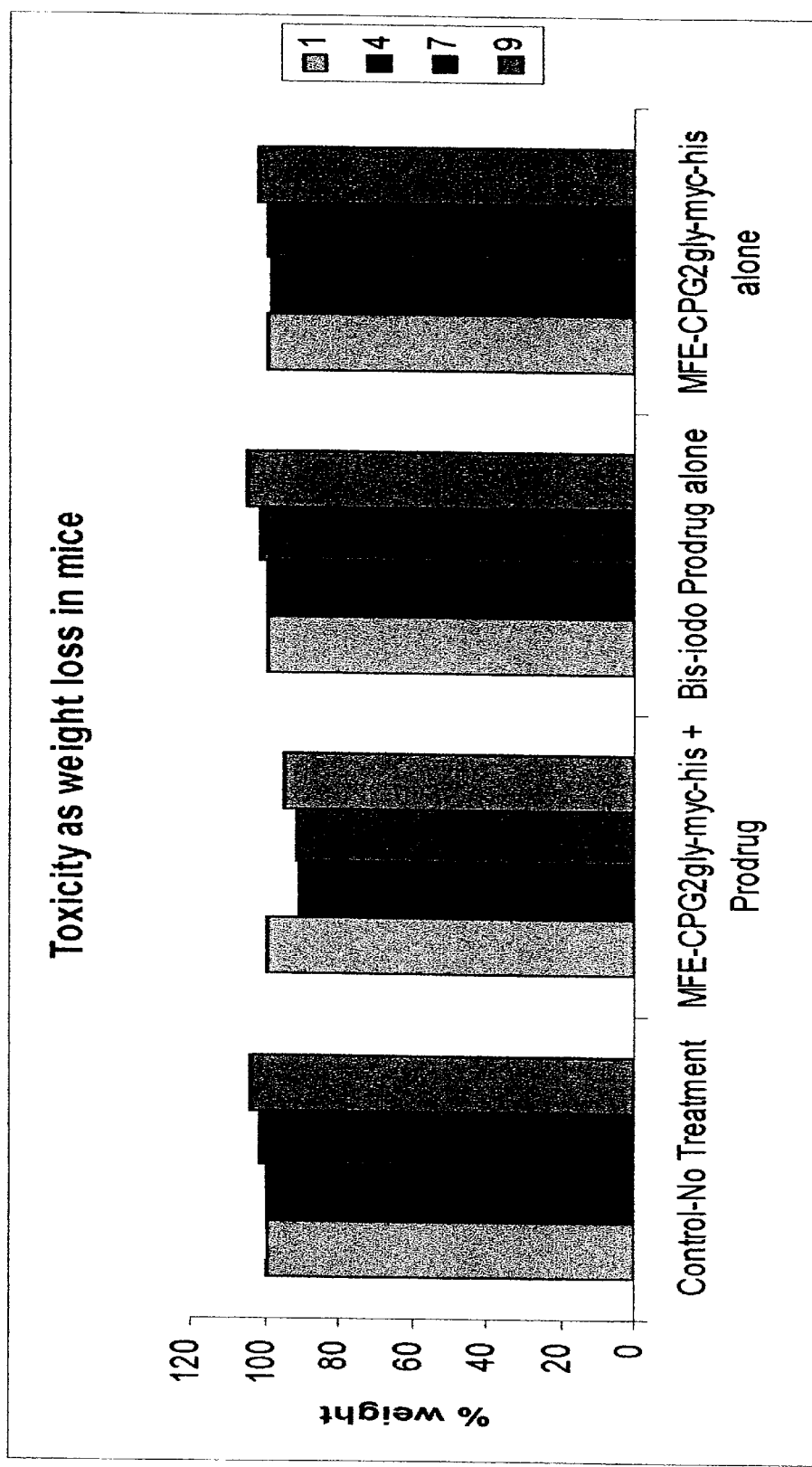
FIG. 11A illustrates toxicity measured as weight loss in LS174T xenografted nude mice given MFE23::CPG-gly-myc-his fusion protein in combination with bis-iodo prodrug.
Figure 11B:
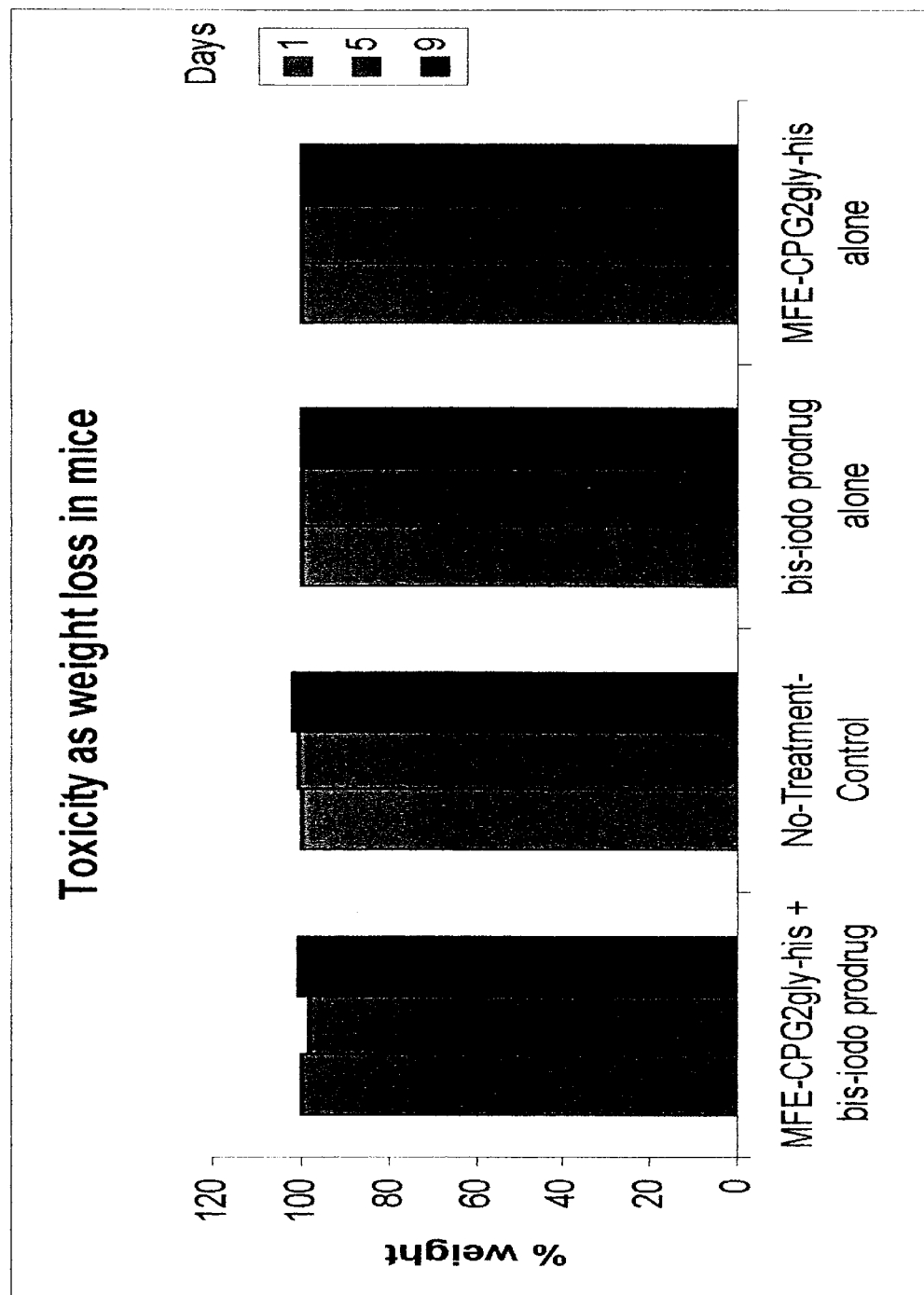
FIG. 11B illustrates toxicity measured as weight loss in LS174T xenografted nude mice given MFE23::CPG-gly-his fusion protein in combination with bis-iodo prodrug.

Mice were weighed prior to treatment and then X2 weekly. Weight % relative to day 1 was calculated for each group of mice. Minimal toxicity was observed, see FIG. 11A for MFE-23::CPG2gly-myc-his and FIG. 11B for MFE-23::CPG2 gly-his.

Example 3

Tagging the CPG2 Protein Reduces Immunogenicity

This example demonstrates that tagging of CPG2 with his or myc-his results in reduced immunogenicity. In particular, MFE-23::CPG2 gly-myc-his has very low immunogenicity.

3.1 Immunogenicity Assay

Balb/C mice (6–8 week old females) were injected with the following fusion proteins (50 ug protein per mouse i.p) at one month intervals.
1. MFE-23::CPG2 gly-myc-his (P. pastoris)
2. MFE-23::CPG2gly-his (P. pastoris)
3. MFE-23::CPG2-his (E. coli)
4. MFE-23::CPG2 (E. coli).

Blood was collected from mice at 14 days post each immunisation. Bloods were tested for mouse anti-CPG2 antibodies by standard ELISA procedures. Briefly, 96-well microtitre plates were coated with 100 μl of CPG2 (10μg/ml in coating buffer) overnight at 4° C. Wells were blocked with 250 μl of 3% BSA for 1 hour and washed with PBS followed by distilled water. Mouse sera (×100 dilution) were incubated in duplicate for 1 hour at RT. Wells were washed with PBS/Tween followed by distilled water and incubated with sheep anti-mouse peroxidase antibody (100 μl/well at 1/500dilution) for one hour. After washing, wells were incubated with substrate (100μl /well) for 5 minutes for colour to develop. The reaction was stopped by addition of 4M HCl. The plate was read at optical density (O.D.)490 nm. SB43gal, a mouse monoclonal anti-CPG2 antibody, was used as a positive control and normal mouse serum was used as a negative control for ELISA reactions. O.D.'s were analysed statistically using a non-parametric test (Mann-Whitney U-test). Results are shown in table 3. (O.D.—optical density, Fp—MFE-23::CPG2 fusion protein, positive control -SB43gal, negative control-normal mouse serum). Results are shown for 10 mice for each fusion protein.

1. After the first immunisation there was no detectable immune response to any of the MFE-23::CPG2 fusion proteins.
2. After the second immunisation there was a detectable immune response to the E.coli expressed MFE-23::CPG2 with no tag (no.4 above) but not to any of the other constructs (nos 1–3 above). This difference was significant (p<0.001).
3. After the third immunisation there was a strong response to MFE-23::CPG2 with no tag, a weaker response to the -his tagged MFE-23::CPG2s (P. pastoris and E coli being similar) and a very low response to the -myc-his tagged MFE-23::CPG2 (see table 3 for details). The differences were significant (p<0.001).
4. After the fourth immunisation there were stronger responses to the -his tagged MFE-23::CPG2s (P. pastoris>E. coli) but still a very low response to the -myc-his tagged MFE-23::CPG2 (see table 3 for details).

The difference between the -myc-his tagged fusion protein and the no tagged fusion protein was significant (p<0.001).

TABLE 3

Plate coated with CPG2

| | Positive | Negative | Fpgly-myc-his | Fpgly-his | e. coli-his | e. coli no tag |
|---|---|---|---|---|---|---|
| Mouse anti-CPG2 response after 1st immunisation | | | | | | |
| O.D. | 0.468 | 0.05 | −0.1 | −0.103 | 0.02 | −0.069 |
| | | | −0.066 | −0.095 | −0.128 | −0.098 |
| | | | −0.068 | −0.091 | −0.076 | −0.046 |
| | | | −0.07 | −0.08 | −0.087 | −0.071 |
| | | | −0.058 | −0.038 | 0.022 | −0.031 |
| | | | −0.091 | −0.077 | −0.073 | −0.068 |
| | | | −0.094 | −0.081 | −0.044 | 0.017 |
| | | | −0.083 | −0.088 | 0.019 | −0.062 |
| | | | −0.041 | −0.104 | −0.052 | −0.098 |
| | | | −0.054 | −0.05 | −0.004 | −0.103 |
| Mouse anti-CPG2 response after 2nd immunisation. | | | | | | |
| O.D. | 0.519 | 0.024 | 0.011 | 0.071 | 0.002 | 0.277 |
| | | | −0.033 | −0.034 | −0.026 | 0.308 |
| | | | −0.055 | −0.035 | 0.011 | 0.198 |
| | | | 0.033 | −0.012 | 0.024 | 0.092 |
| | | | −0.017 | 0.05 | −0.025 | 0.228 |
| | | | −0.012 | −0.028 | 0.083 | 0.315 |
| | | | −0.01 | −0.056 | −0.009 | 0.232 |
| | | | −0.03 | −0.041 | 0.078 | 0.313 |
| | | | −0.003 | −0.043 | 0.023 | −0.015 |
| | | | −0.023 | −0.027 | 0.034 | 0.116 |
| Mouse anti-CPG2 response after 3rd immunisation | | | | | | |
| O.D. | 1.167 | 0.02 | 0.019 | 0.897 | 0.801 | 1.709 |
| | | | 0.222 | 0.514 | 1.4 | 1.618 |
| | | | 0.028 | 0.095 | 0.794 | 1.374 |
| | | | 0.005 | 0.98 | 1.436 | 1.289 |
| | | | 0.015 | 1.67 | 1.19 | 1.904 |
| | | | 0.02 | 0.454 | 1.344 | 1.722 |
| | | | 0.029 | 0.984 | 0.952 | 1.884 |
| | | | 0.021 | 0.791 | 1.202 | 1.775 |
| | | | 0.039 | 0.55 | 0.86 | 1.077 |
| | | | 0.025 | 1.416 | 1.523 | 1.454 |
| Mouse anti-CPG2 response after 4th immunisation | | | | | | |
| O.D. | 0.91 | 0.005 | 0.037 | 0.565 | 1.156 | 1.293 |
| | | | 0.738 | 0.691 | 1.064 | 1.316 |
| | | | 0.058 | 0.198 | 1.14 | 1.188 |
| | | | 0.038 | 1.591 | 1.14 | 0.765 |
| | | | 0.09 | 1.182 | 0.934 | 1.208 |
| | | | 0.244 | 1.463 | 1.011 | 1.415 |
| | | | 0.13 | 1.509 | 1.17 | 1.484 |
| | | | 0.314 | 0.931 | 0.9 | 1.116 |
| | | | 0.083 | 1.235 | 0.412 | 1.389 |
| | | | 0.109 | 1.202 | 0.693 | 1.198 |

Negative numbers are below detection limits.
Immune response to E. coli and P. pastoris produced MFE-23 CPG2 with different tags In conclusion, there is a difference in immunogenicity between the tagged and non-tagged fusion proteins; -his tag being slightly effective in reducing the immune response and -myc-his tag being very effective.

The reduction in immunogenicity is apparently not due to glycosylation as there is no significant difference between the immune response to MFE-23::CPG2-his tagged fusion proteins from E.coli (not glycosylated) and P. pastoris (glycosylated).

3.2 Molecular Dynamic Modelling

Figure 12:
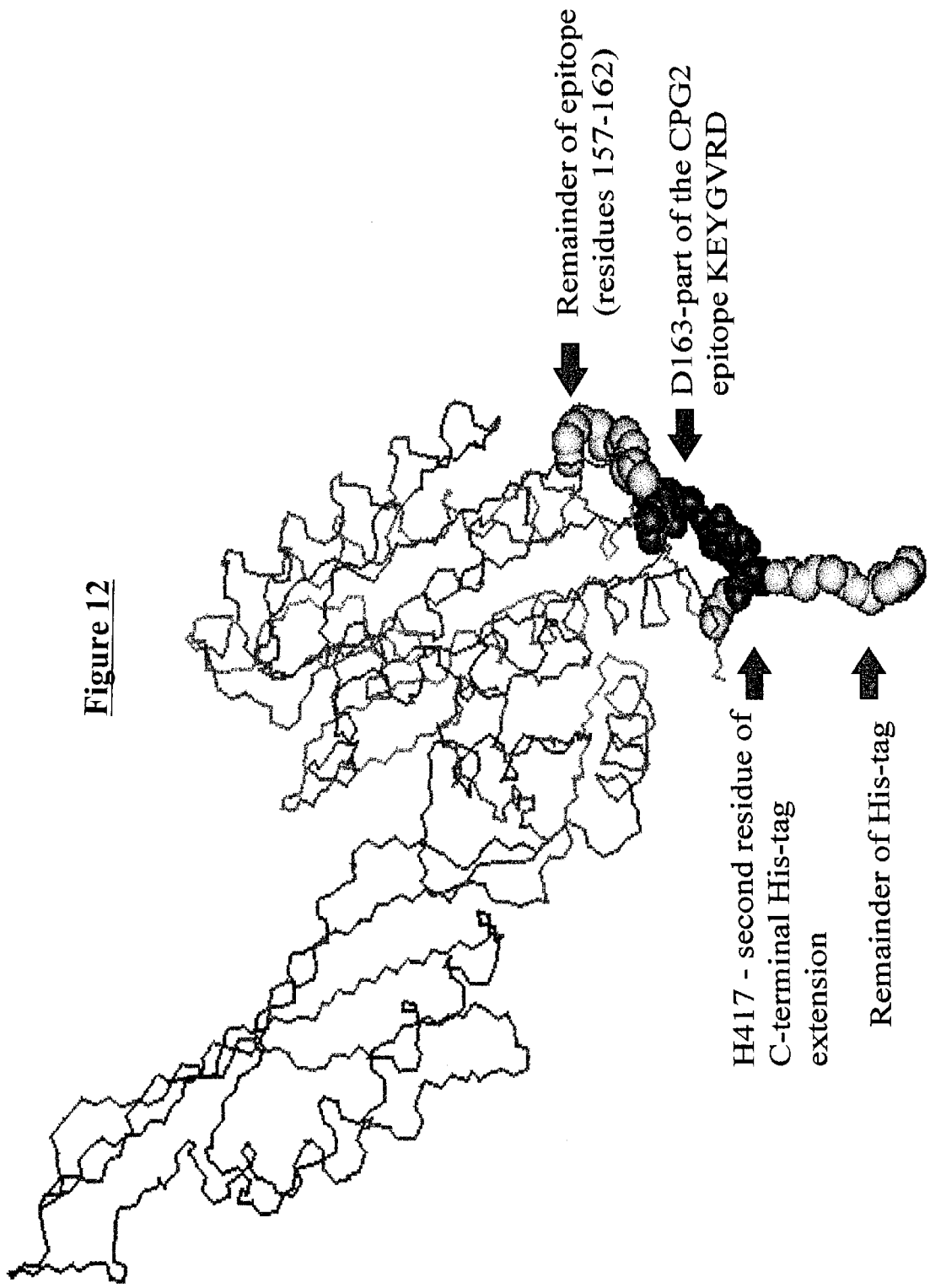
FIG. 12 illustrates the CPG2 molecule showing the molecular dynamics predicted interaction of a charged histidine residue in the hexa-His-tag with a residue from the epitope KEYGVRD, residues 157–163.
Figure 13:
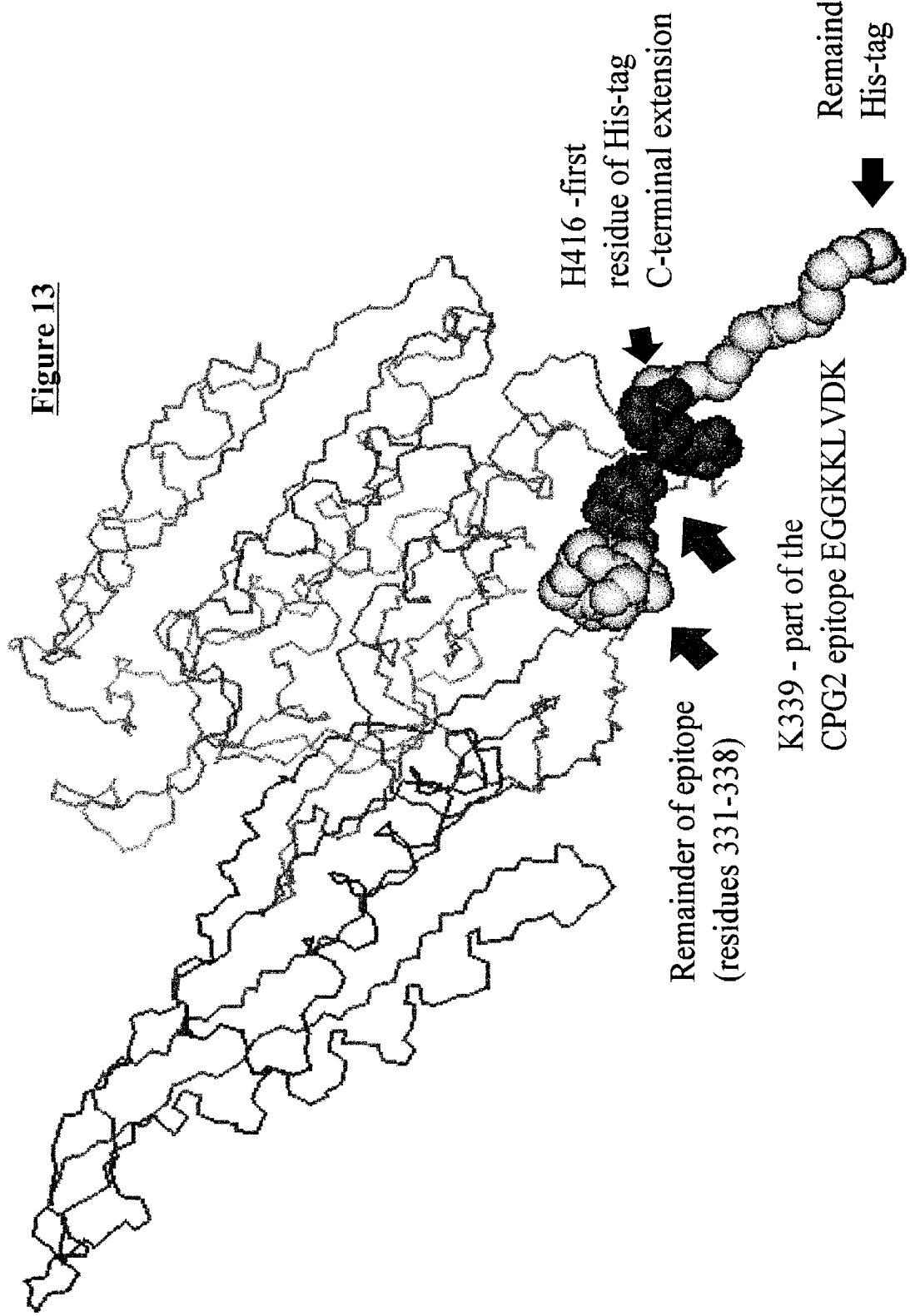
FIG. 13 illustrates the CPG2 molecule (chain A only) showing the molecular dynamics predicted interaction of an uncharged histidine residue in the hexa-His-tag with a residue from the epitope EGGKKLVDK, residues 331–339, the prediction assuming an uncharged His-tag.
Figure 14:
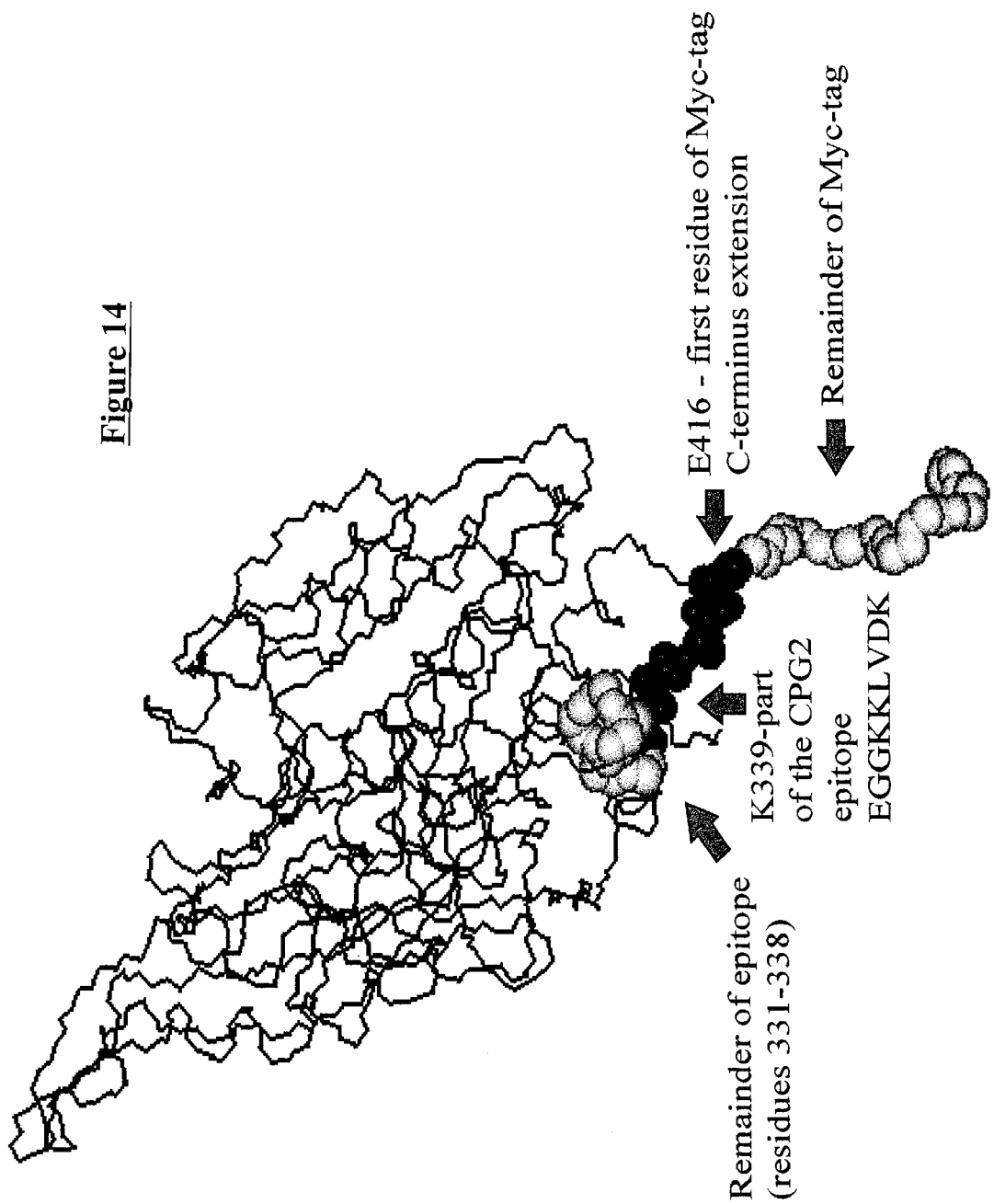
FIG. 14 illustrates the CPG2 molecule (chain A only) showing the molecular dynamics predicted interaction of a glutamate residue in the Myc tag with a residue from the epitope EGGKKLVDK, residues 331–339.

Molecular dynamic modelling was used to simulate the interaction of His-tags and Myc-tags with the CPG2 molecule. The results are shown in FIGS. 12, 13 and 14. FIG. 12 shows that a charged histidine residue in the hexa-His tag may interact with a residue (residue 163) from the epitope KEYGVRD(residues 157–163). Such interaction would explain the reduced immunogenicity seen when such tags are used. FIG. 13 shows that an uncharged histidine residue in the hexa-His tag may interact with a residue (residue K339) from the epitope EGGKKLVDK(residues 331–339). FIG. 14 shows that an a glutamate residue in the Myc tag may interact with a residue (residue K339) from the epitope EGGKKLVDK(residues 331–339). The modelling supports the observation that the tags reduce immunogenicity.

We claim:

1. An isolated carboxypeptidase enzyme, CPG2, in which an immunogenic region is modified to reduce immunogenicity to a mammalian immune system whilst retaining CPG2 activity, wherein the immunogenic region is selected from the group consisting of: (i) KIKGRGGK (SEQ ID NO:1) comprising residues 98–105 of SEQ ID NO:7, (ii) KEYGVRD (SEQ ID NO:2) comprising residues 157–163 of SEQ ID NO:7, (iii) YGVRD (SEQ ID NO:6) comprising residues 159–163 of SEQ ID NO:7, (iv) KLADY (SEQ ID NO:3), comprising residues 191–195 of SEQ ID NO:7, (v) GAGK (SEQ ID NO:4), comprising residues 412 to the C-terminal residue 415 of SEQ ID NO:7, (vi) AG comprising residues 413–414 of SEQ ID NO:7, and (vii) EGGKKLVDK (SEQ ID NO:5) comprising residues 331–339 of SEQ ID NO:7, wherein said enzyme is fused to an anti-CEA antibody.

2. An isolated or purified Pseudomonas carboxypeptidase CPG2 enzyme wherein the C-terminus of the enzyme comprises an extension selected from the group consisting of a histidine tag, a myc tag, and a myc-his tag and wherein said CPG2 enzyme is fused to an anti-CEA antibody.

3. An isolated carboxypeptidase enzyme, CPG2, in which an immunogenic region is modified to reduce immunogenicity to a mammalian immune system whilst retaining CPG2 activity, wherein the immunogenic region is selected from the group consisting of:

KIKGRGGK (SEQ ID NO:1) comprising residues 98–105 of SEQ ID NO:7);

(ii) KEYGVRD (SEQ ID NO:2) comprising residues 157–163 of SEQ ID NO:7;

(iii) YGVRD (SEQ ID NO:6) comprising residues 159–163 of SEQ ID NO:7;

(iv) KLADY (SEQ ID NO:3) comprising residues 191–195 of SEQ ID NO:7;

(v) GAGK (SEQ ID NO:4) comprising residues 412 to the C-terminal residue 415 of SEQ ID NO:7;

(vi) AG comprising residues 413–414 of SEQ ID NO:7; and (vii) EGGKKLVDK (SEQ ID NO:5) comprising residues 331–339 of SEQ ID NO:7;

wherein said enzyme is fused to an anti-CEA antibody; and wherein the C-terminus of the enzyme comprises an extension selected from the group consisting of a histidine tag, a myc tag and a myc-his tag.

4. The carboxypeptidase enzyme of claim 1 or 2 wherein said anti-CEA antibody is MFE23.

5. A method of preparing a fusion protein comprising a carboxypeptidase CPG2 enzyme of claim 1 or claim 2 or claim 3 wherein the C-terminus of the enzyme comprises an extension selected from the group consisting of a histidine tag, a myc tag, and a myc-his tag, said method comprising expressing a DNA sequence encoding said fusion operably linked to a promoter in a *Pichia pastoris* host cell, and recovering said fusion protein therefrom.

6. The method of claim 5 wherein said antibody is MFE23.

7. A kit comprising a first component which is a prodrug which can be converted to a cytotoxic drug by a carboxypeptidase of claim 1; and, as a second component, said carboxypeptidase.

8. The carboxypeptidase enzyme of claim 3 wherein said anti-CEA antibody is MFE23.

9. A kit comprising a first component which is a prodrug which can be converted to a cytotoxic drug by a carboxypeptidase of claim 2; and, as a second component, said carboxypeptidase.

10. A kit comprising a first component which is a prodrug which can be converted to a cytotoxic drug by a carboxypeptidase of claim 3; and, as a second component, said carboxypeptidase.

* * * * *

SEQUENCE LISTING

```
<160> NUMBER OF SEQ ID NOS: 21

<210> SEQ ID NO 1
<211> LENGTH: 8
<212> TYPE: PRT
<213> ORGANISM: Pseudomonas sp.

<400> SEQUENCE: 1

Lys Ile Lys Gly Arg Gly Gly Lys
  1               5

<210> SEQ ID NO 2
<211> LENGTH: 7
<212> TYPE: PRT
<213> ORGANISM: Pseudomonas sp.

<400> SEQUENCE: 2

Lys Glu Tyr Gly Val Arg Asp
  1               5

<210> SEQ ID NO 3
<211> LENGTH: 5
<212> TYPE: PRT
<213> ORGANISM: Pseudomonas sp.

<400> SEQUENCE: 3

Lys Leu Ala Asp Tyr
  1               5

<210> SEQ ID NO 4
<211> LENGTH: 4
<212> TYPE: PRT
<213> ORGANISM: Pseudomonas sp.

<400> SEQUENCE: 4

Gly Ala Gly Lys
  1

<210> SEQ ID NO 5
<211> LENGTH: 9
<212> TYPE: PRT
<213> ORGANISM: Pseudomonas sp.

<400> SEQUENCE: 5

Glu Gly Gly Lys Lys Leu Val Asp Lys
  1               5

<210> SEQ ID NO 6
<211> LENGTH: 5
<212> TYPE: PRT
<213> ORGANISM: Pseudomonas sp.

<400> SEQUENCE: 6

Tyr Gly Val Arg Asp
  1               5

<210> SEQ ID NO 7
<211> LENGTH: 415
```

```
<212> TYPE: PRT
<213> ORGANISM: Pseudomonas sp.

<400> SEQUENCE: 7

Met Arg Pro Ser Ile His Arg Thr Ala Ile Ala Ala Val Leu Ala Thr
 1               5                  10                  15

Ala Phe Val Ala Gly Thr Ala Leu Ala Gln Lys Arg Asp Asn Val Leu
             20                  25                  30

Phe Gln Ala Ala Thr Asp Glu Gln Pro Ala Val Ile Lys Thr Leu Glu
         35                  40                  45

Lys Leu Val Asn Ile Glu Thr Gly Thr Gly Asp Ala Glu Gly Ile Ala
     50                  55                  60

Ala Ala Gly Asn Phe Leu Glu Ala Glu Leu Lys Asn Leu Gly Phe Thr
 65                  70                  75                  80

Val Thr Arg Ser Lys Ser Ala Gly Leu Val Gly Asp Asn Ile Val
                 85                  90                  95

Gly Lys Ile Lys Gly Arg Gly Lys Asn Leu Leu Met Ser His
                100                 105                 110

Met Asp Thr Val Tyr Leu Lys Gly Ile Leu Ala Lys Ala Pro Phe Arg
            115                 120                 125

Val Glu Gly Asp Lys Ala Tyr Gly Pro Gly Ile Ala Asp Asp Lys Gly
        130                 135                 140

Gly Asn Ala Val Ile Leu His Thr Leu Lys Leu Leu Lys Glu Tyr Gly
145                 150                 155                 160

Val Arg Asp Tyr Gly Thr Ile Thr Val Leu Phe Asn Thr Asp Glu Glu
                165                 170                 175

Lys Gly Ser Phe Gly Ser Arg Asp Leu Ile Gln Glu Glu Ala Lys Leu
            180                 185                 190

Ala Asp Tyr Val Leu Ser Phe Glu Pro Thr Ser Ala Gly Asp Glu Lys
        195                 200                 205

Leu Ser Leu Gly Thr Ser Gly Ile Ala Tyr Val Gln Val Asn Ile Thr
210                 215                 220

Gly Lys Ala Ser His Ala Gly Ala Ala Pro Glu Leu Gly Val Asn Ala
225                 230                 235                 240

Leu Val Glu Ala Ser Asp Leu Val Leu Arg Thr Met Asn Ile Asp Asp
                245                 250                 255

Lys Ala Lys Asn Leu Arg Phe Asn Trp Thr Ile Ala Lys Ala Gly Asn
            260                 265                 270

Val Ser Asn Ile Ile Pro Ala Ser Ala Thr Leu Asn Ala Asp Val Arg
        275                 280                 285

Tyr Ala Arg Asn Glu Asp Phe Asp Ala Ala Met Lys Thr Leu Glu Glu
    290                 295                 300

Arg Ala Gln Gln Lys Lys Leu Pro Glu Ala Asp Val Lys Val Ile Val
305                 310                 315                 320

Thr Arg Gly Arg Pro Ala Phe Asn Ala Gly Glu Gly Lys Lys Leu
                325                 330                 335

Val Asp Lys Ala Val Ala Tyr Tyr Lys Glu Ala Gly Gly Thr Leu Gly
            340                 345                 350

Val Glu Glu Arg Thr Gly Gly Thr Asp Ala Ala Tyr Ala Ala Leu
        355                 360                 365

Ser Gly Lys Pro Val Ile Glu Ser Leu Gly Leu Pro Gly Phe Gly Tyr
    370                 375                 380

His Ser Asp Lys Ala Glu Tyr Val Asp Ile Ser Ala Ile Pro Arg Arg
385                 390                 395                 400
```

```
Leu Tyr Met Ala Ala Arg Leu Ile Met Asp Leu Gly Ala Gly Lys
            405                 410                 415
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: myc tag

<400> SEQUENCE: 8

```
Glu Gln Lys Leu Ile Ser Glu Glu Asp Leu Asn
 1               5                  10
```

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence:
      myc-his tag

<400> SEQUENCE: 9

```
Ala Ala Ala Ser Phe Leu Glu Gln Lys Leu Ile Ser Glu Glu Asp Leu
 1               5                  10                  15

Asn Ser Ala Val Asp His His His His His His
            20                  25
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Hybrid
      sequence

<400> SEQUENCE: 10

```
Tyr Glu Tyr Gly Val Met Lys
 1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Humanised
      sequence

<400> SEQUENCE: 11

```
Tyr Glu Val Gly Met Met Lys
 1               5
```

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Hybrid
      sequence

<400> SEQUENCE: 12

```
Arg Asn Ser Asp Tyr
 1               5
```

<210> SEQ ID NO 13
<211> LENGTH: 5

```
<212> TYPE: PRT
<213> ORGANISM: Artificial Sequence
<220> FEATURE:
<223> OTHER INFORMATION: Description of Artificial Sequence: Humanised
      sequence

<400> SEQUENCE: 13

Arg Asn Ser Asp Arg
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:
      CPG2 variant

<400> SEQUENCE: 14

Ala Glu Tyr Gly Val Arg Asp
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:
      CPG2 variant

<400> SEQUENCE: 15

Lys Ala Tyr Gly Val Arg Asp
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:
      CPG2 variant

<400> SEQUENCE: 16

Lys Glu Ala Gly Val Arg Asp
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:
      CPG2 variant

<400> SEQUENCE: 17

Lys Glu Tyr Ala Val Arg Asp
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      CPG2 variant

<400> SEQUENCE: 18

Lys Glu Tyr Gly Ala Arg Asp
```

-continued 1 5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: CPG2 variant

<400> SEQUENCE: 19

Lys Glu Tyr Gly Val Ala Asp
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: CPG2 variant

<400> SEQUENCE: 20

Lys Glu Tyr Gly Val Arg Ala
1 5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: CPG2 variant

<400> SEQUENCE: 21

Ala Ala Gly Lys
1